United States Patent [19]

Kobayashi et al.

[11] Patent Number: 5,131,059
[45] Date of Patent: Jul. 14, 1992

[54] IMAGE SIGNAL PROCESSOR

[75] Inventors: Kazuto Kobayashi, Tokyo; Shinichi Sato, Yokohama, both of Japan

[73] Assignee: Matsushita Graphic Communication Systems, Inc., Tokyo, Japan

[21] Appl. No.: 416,325

[22] Filed: Oct. 2, 1989

[30] Foreign Application Priority Data

Sep. 30, 1988 [JP] Japan .................. 63-248244

[51] Int. Cl.$^5$ ................ G06K 9/38
[52] U.S. Cl. .................. 382/50; 358/429; 358/456
[58] Field of Search .......... 382/50, 18, 48, 56, 382/51, 52, 53, 62; 358/429, 460, 456, 457, 455, 463; 364/518, 519, 523, 521

[56] References Cited

U.S. PATENT DOCUMENTS

| 4,194,221 | 12/1978 | Stoffel | 358/456 |
|---|---|---|---|
| 4,707,745 | 11/1987 | Sakano | 382/50 |
| 4,821,334 | 4/1989 | Ogino et al. | 382/50 |
| 4,920,501 | 4/1990 | Sullivan et al. | 382/52 |
| 4,924,509 | 3/1989 | Yokomizo | 382/50 |

Primary Examiner—Michael Razavi
Attorney, Agent, or Firm—Wenderoth, Lind & Ponack

[57] ABSTRACT

An image signal processor includes a first processing unit for carrying out a predetermined first quasi-tone reproduction process on an input image signal and for outputting a corresponding first processed image signal, a second processing unit for low-pass filter processing the input signal and for carrying out a predetermined second quasi-tone reproduction process on the thus low-pass filter processed input image signal and for outputting a corresponding second processed image signal, and a binarization processing unit for converting the input image signal into a binary image signal and for outputting the binary image signal. An image signal identification unit is provided for outputting an identification signal representative of a type of the input image signal based on a detected power level of the input image signal at each of at least one fixed frequency in at least one of a main scanning direction in which a read sensor for scanning image information of a document is arranged and a subscanning direction in which a read sensor is moved relative to the document. A selection unit is provided for outputting in accordance with the identification signal one of the first processed image signal of the first processing unit, the second processed image signal of the second processing unit and the binary image signal of the binarization processing unit.

22 Claims, 24 Drawing Sheets

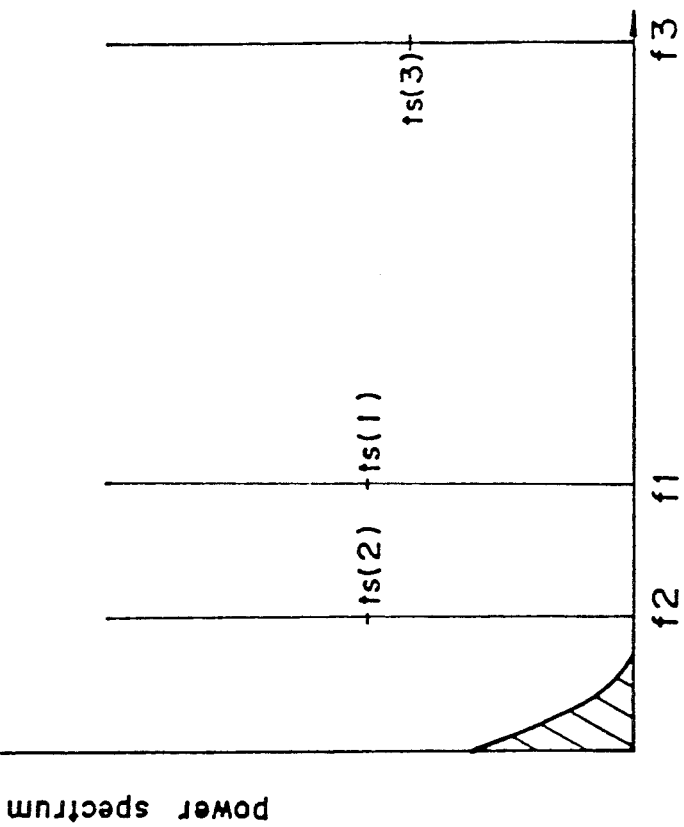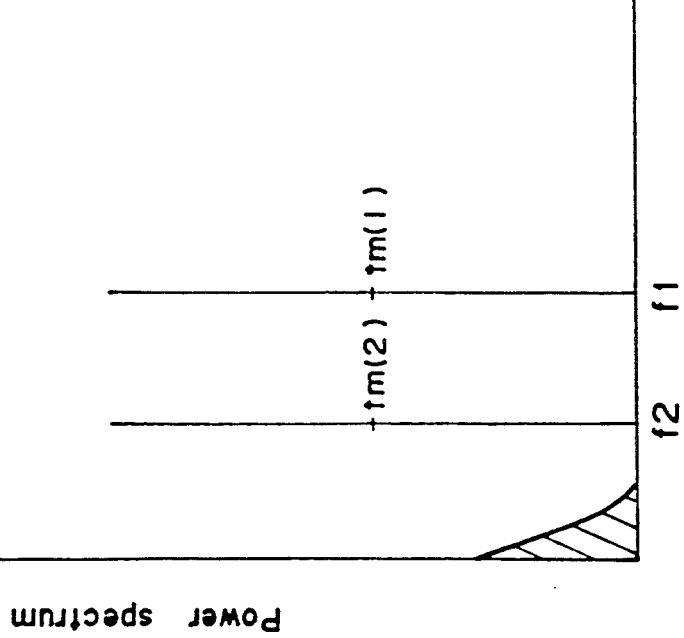

ds(1)=0
ds(2)=0
ds(3)=0 dm(1)=1
dm(2)=1
dm(3)=1

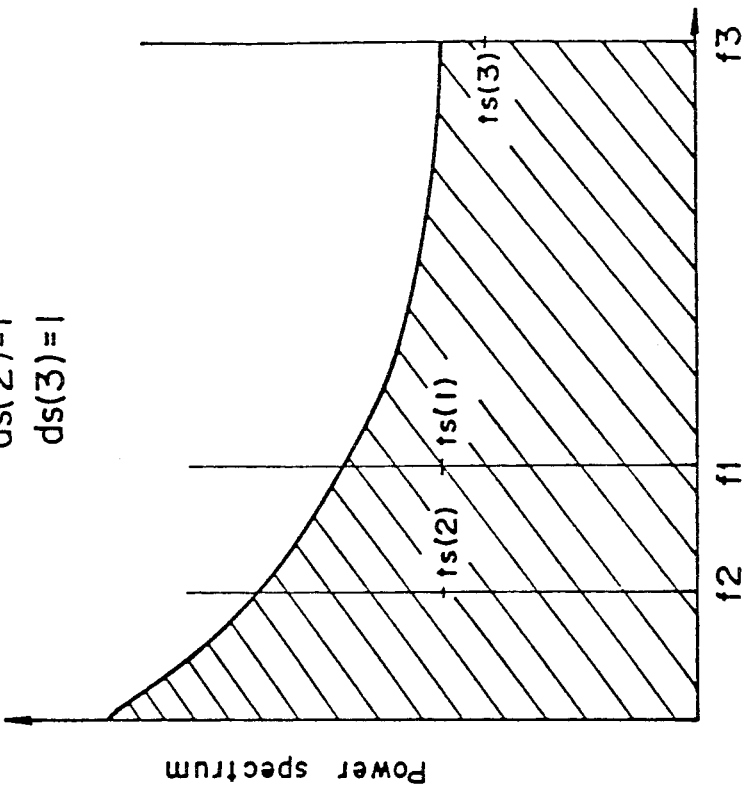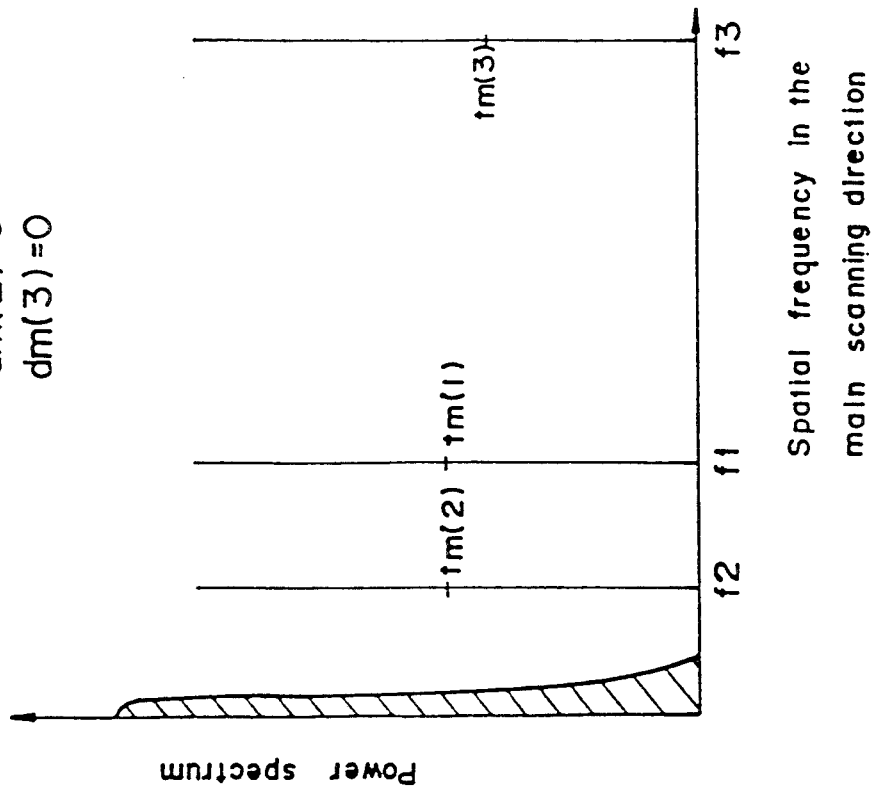

dm(1)=1
dm(2)=0
dm(3)=0 ds(1)=0
ds(2)=0
ds(3)=0 dm(1)=0
dm(2)=0
dm(3)=0 ds(1)=1
ds(2)=0
ds(3)=0

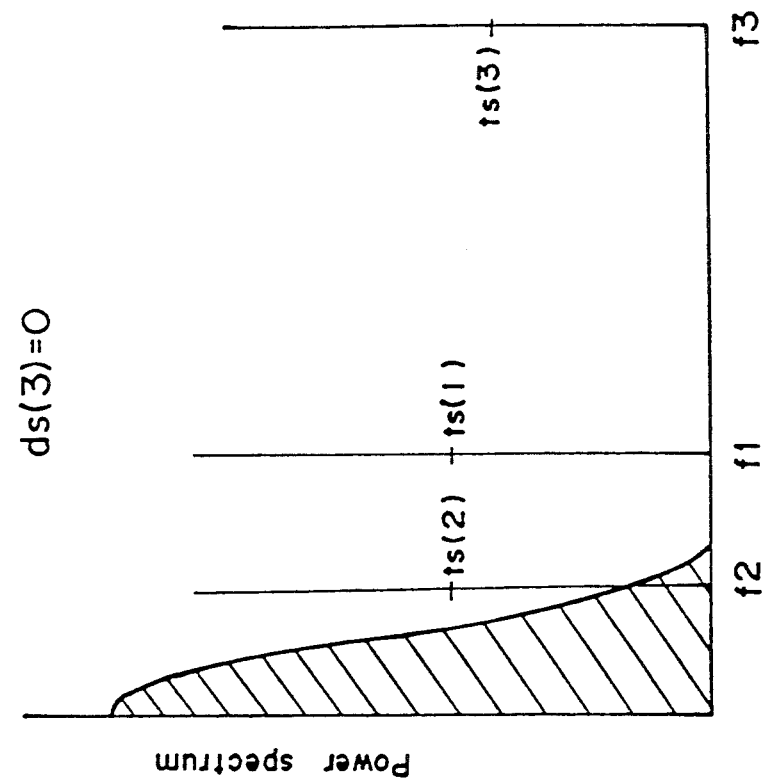
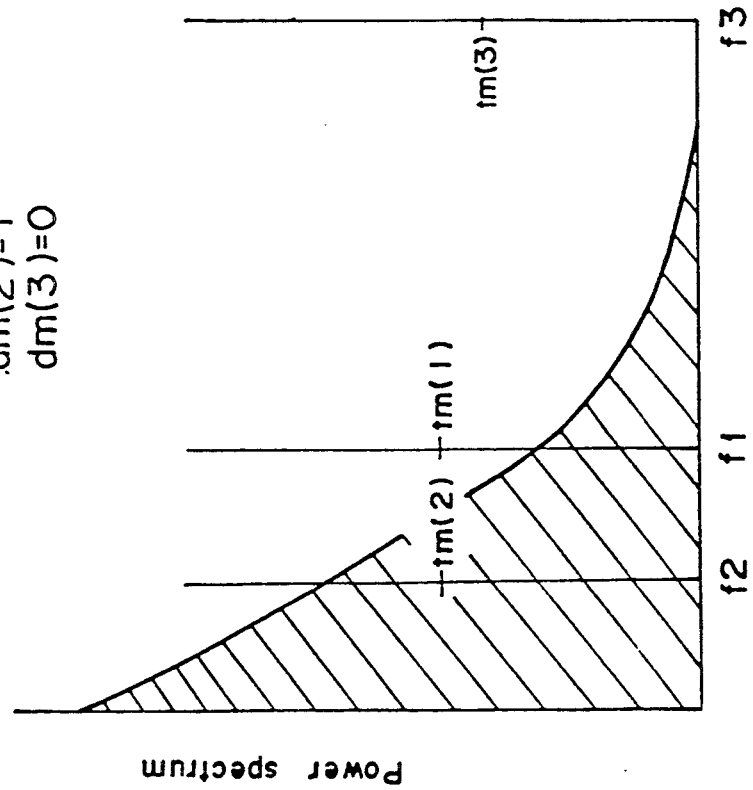

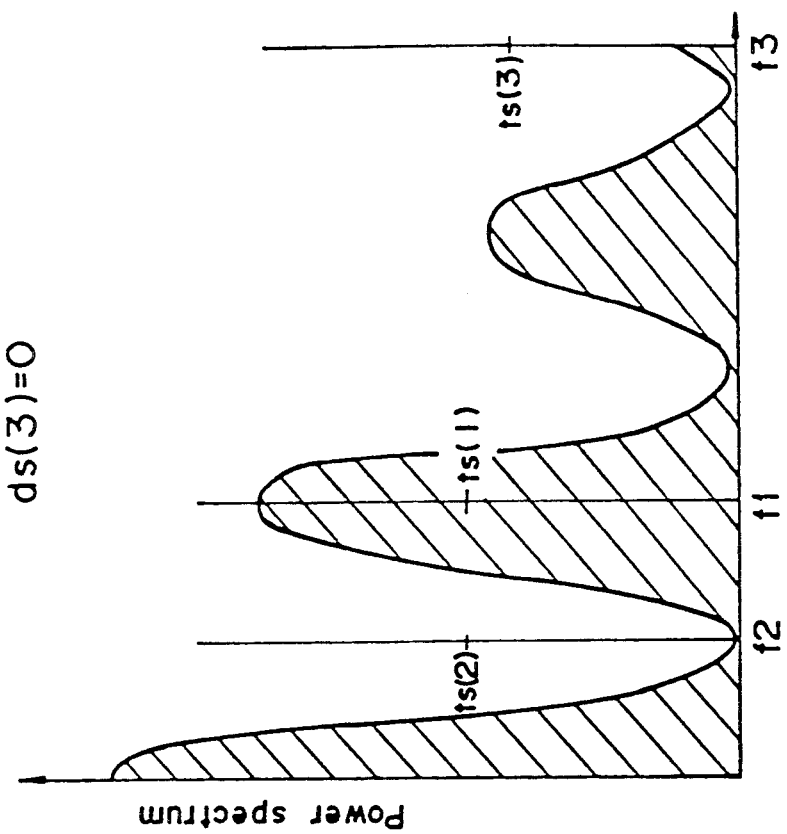
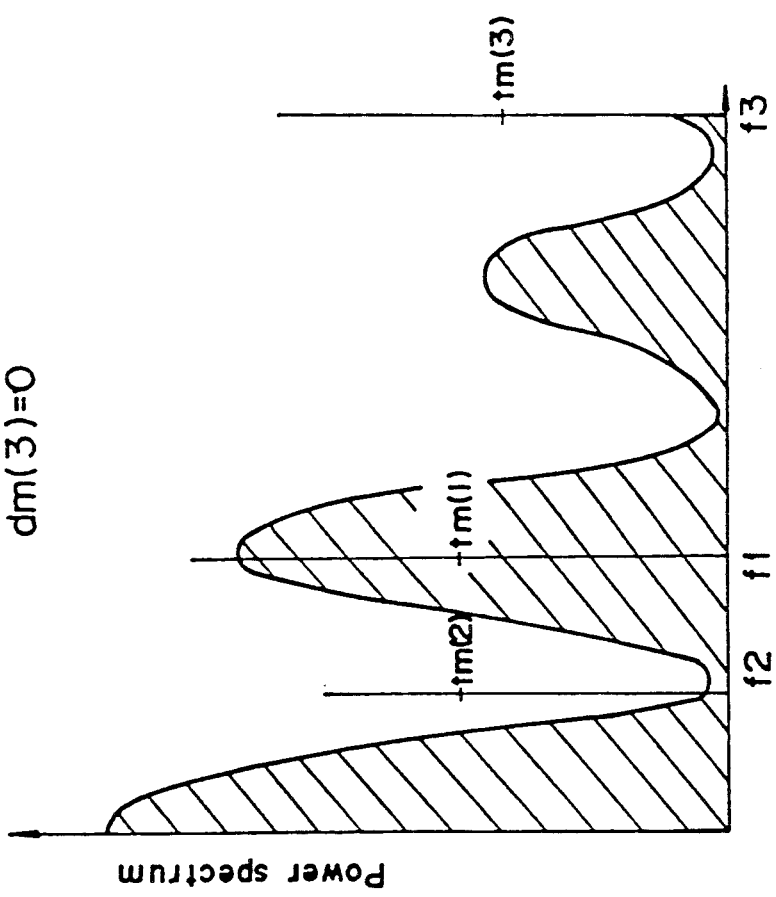

IMAGE SIGNAL PROCESSOR

BACKGROUND OF THE INVENTION

The present invention relates to an image signal processor for a facsimile device, a copying machine, etc., and more particularly, to an image signal processor which performs a proper image process for each type of image signal. When a digitized input image signal of a manuscript in which halftone images of a character, a photograph and a screen halftone are mixed is uniformly binarized, the gradation of the halftone images is not reproduced. When a quasi-tone reproduction process, which is represented by a dither process, is uniformly executed for the image input signals, characters become obscure or blurred. This is because of the fact that the binarization is originally a process suitable for a character, and a quasi-tone reproduction process is suitable for a halftone image. It is therefore necessary to execute a proper process upon identifying the type of an input image. An image processor having an image signal identification device which accurately identifies the type of input image is needed for this purpose.

In a Japanese patent application laid-open No. 80965/1986, an image identification method is disclosed as follows. Inside a block surrounding a picture element to be identified, a plurality of density difference values between pairs of fixed picture elements is detected, and if a maximum value among these density gradient values is larger than a certain threshold value, the picture element is identified to be a character, and if the maximum value of density gradient values is smaller than the certain threshold value, the picture element is identified to be a halftone image.

When a method of this kind is used, there is a possibility that a screen halftone will be mistaken for a character. Since a screen halftone is originally an image recorded with white and black dots on a sheet of paper, when a manuscript is read, the maximum value of the density difference in a block can be as large as that of a character. It is therefore difficult to distinguish a character from a screen halftone based solely on the density difference. Furthermore, when a screen halftone is dither-processed, moire stripes (a periodic density change which is not found in a manuscript) are produced.

SUMMARY OF THE INVENTION

An object of the present invention is to provide an image signal processor which identifies the type of an input image having a mixture of a characters and halftone images, and which executes a proper image process for each type of identified input image.

Another object of the present invention is to provide an image signal processor in which the occurrence of moire stripes of a screen halftone is suppressed without deteriorating the input quality of a character or a photograph.

An image signal processor according to the present invention includes an image signal process means for executing a proper process for each type of input image signal, an image signal identification means for outputting a identification (type) signal of the input image signal based on a detected power at a fixed frequency in the main scanning direction or in the subscanning direction of the input signal, and a selection means for selecting the output of an image process means suited for an input image signal.

BRIEF DESCRIPTION OF THE DRAWINGS

FIG. 3A is a spatial frequency distribution chart in the main scanning direction of a flat part of a character.

FIG. 3B is a spatial frequency distribution chart in the subscanning direction of a flat part of a character.

FIG. 5A is a spatial frequency distribution chart in the main scanning direction of a character having an edge in the subscanning direction.

FIG. 5B is a spatial frequency distribution chart in the subscanning direction of a character having an edge in the subscanning direction.

FIG. 9A is a spatial frequency distribution chart in the main scanning direction of a photograph having an edge in the main scanning direction.

FIG. 9B is a spatial frequency distribution chart in the subscanning direction of a photograph having an edge in the main scanning direction.

FIG. 11A is a spatial frequency distribution chart in the main scanning direction of a flat part of a screen halftone.

FIG. 11B is a spatial frequency distribution chart in the subscanning direction of a flat part of a screen halftone.

DESCRIPTION OF THE PREFERRED EMBODIMENTS

Figure 1:
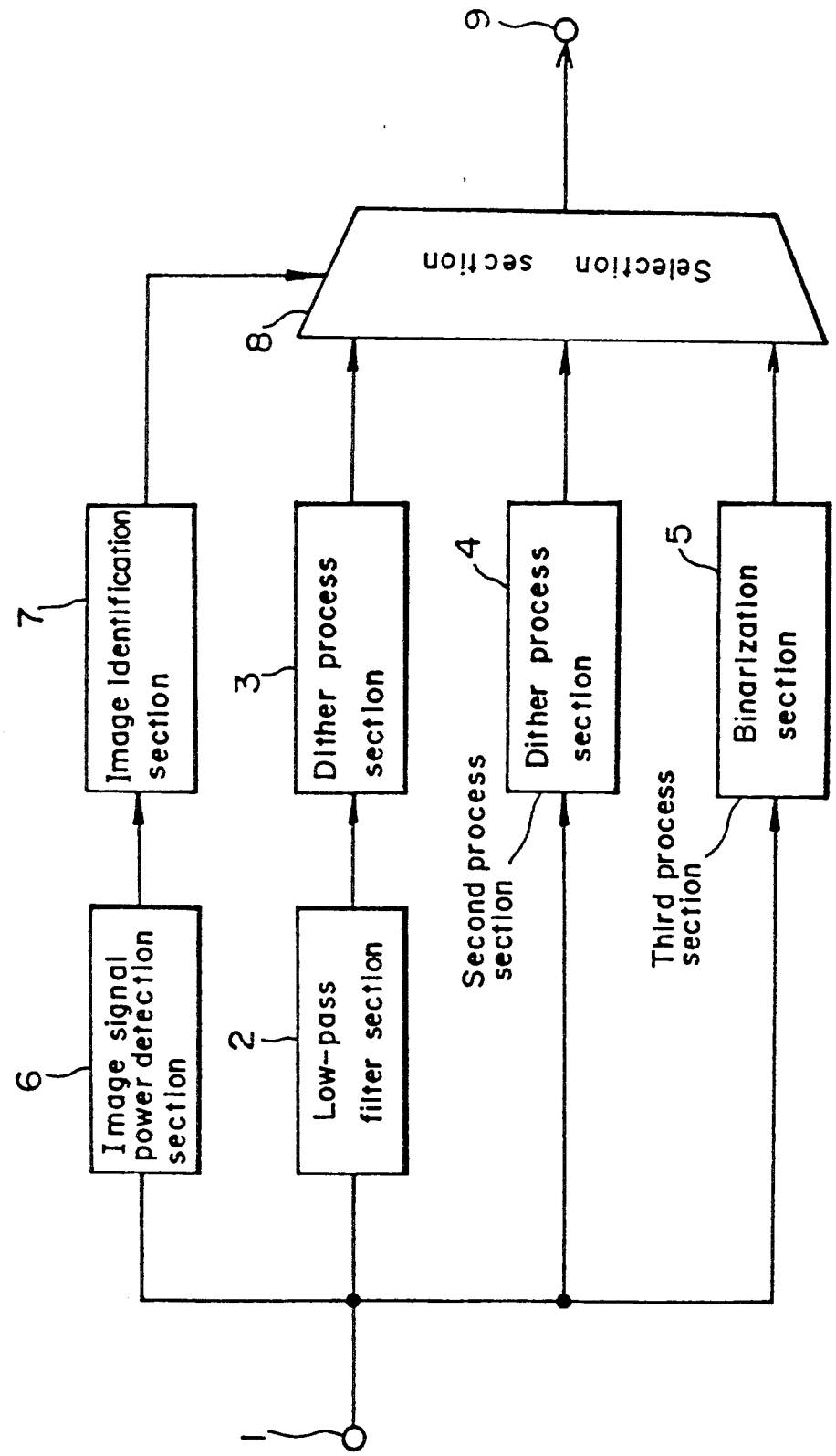
FIG. 1 is a block diagram of a first embodiment of the present invention.

The preferred embodiments of the present invention will be described below referring to the drawings.

FIG. 1 shows a first embodiment of the present invention.

As shown in FIG. 1, a digitized image signal is input to an input terminal 1. The input image signal is filter-processed in a low-pass filter section 2 and and the thus filter-processed signal is dither-processed in a dither process section 3. The image signal is also directly input to a dither process section 4 to be dither-processed. The image signal is also input to a binarization process section 5 to be binarized. The image signal is also input to a detection section 6 and the power at a fixed frequency of the image signal is detected. An image identification section 7 outputs a selection signal corresponding to the detected power of the image signal. A selection section 8 selects an output from the outputs of the dither process section 3, the dither process section 4 or the binarization section 5 based on the selection signal, and outputs the selected output to an output terminal 9.

The low-pass filter 2 and the dither process section 3 correspond to a first process means, and the image signal power detection section 6 and the image identification section 7 correspond to an image signal identification means.

Figure 2:
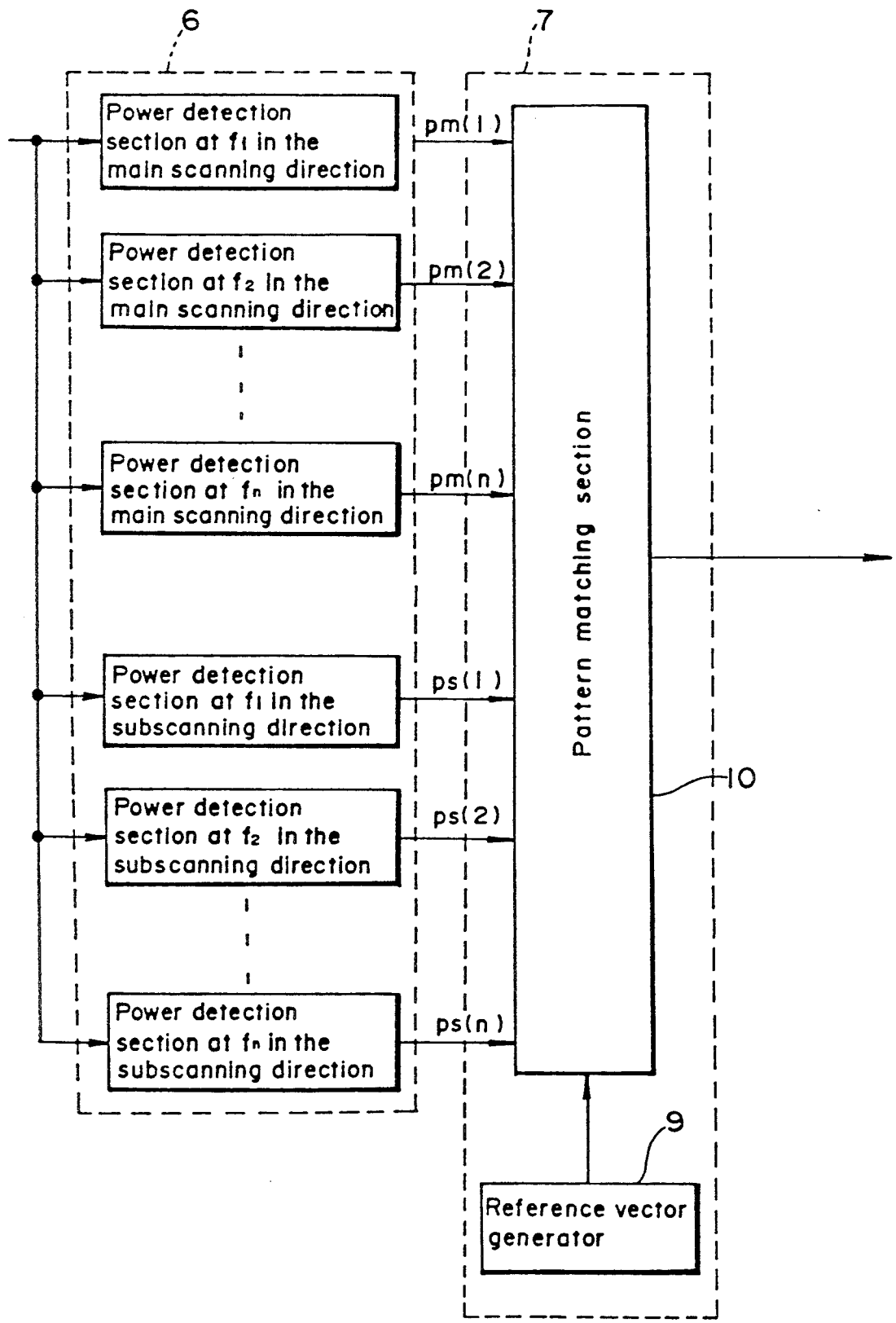
FIG. 2 is a detailed drawing of an image signal power detection section and an image identification section shown in FIG. 1.

FIG. 2 is a detailed drawing showing the image signal power detection section 6 and the image identification section 7.

The image signal power detection section 6 is constituted so that an fi power detection section 60$i$ in the main scanning direction, which detects the power pm(i) (i=1 to n) at a fixed frequency fi in the main scanning direction, and an fi power detection section 61$i$ in the subscanning direction, which detects the power ps(i) (i=1 to n) at a fixed frequency fi in the subscanning direction, are connected in parallel to the input terminal 1. The image identification section 7 is constituted by a reference vector generation section 9, which generates a selection criteria reference signal, and a pattern matching section 10, which outputs a selection signal based on the reference signal and the power pm(i) and ps(i).

The description on of the operation of the first embodiment is set forth below.

An image signal input from the input terminal 1 is input respectively to the low-pass filter section 2, the dither process section 4, the binarization section 5 and the image signal power detection section 6. The low-pass filter section 2 removes the mesh point structure of a screen halftone using a filter. The reason for this is that when a screen halftone is directly dither-processed moire stripes are produced as mentioned above. As such, filtering is needed for the prevention of moire stripes. The dither process section 3 dither-processes an image signal processed using the low-pass filter 2 and outputs the filtered dither-processed signal to the selection section 8. The dither process section 4 dither-processes the input image signal and outputs the dither-processed input image signal to the selection section 8. The binarization section binarizes the input image signal using a fixed threshold value and outputs the binarized signal to the selection section 8. The image signal power detection section 6 detects the power pm(i) of the image signal at a fixed frequency fi in the main scanning direction using the fi power detector 60$i$ in the main scanning direction, and detects the power ps(i) of the image signal at a frequency fi in the subscanning direction using the fi power detector 61$i$ in the subscanning direction, and outputs the detected powers pm(i) and ps(i) to a pattern matching section 10. The pattern matching section 10 identifies the type of input image to be that of a character, a photograph or a screen halftone. In principle, when the image input is identified to be a character, the output of the binarization section 5 is supplied to the output terminal 9, when the input is identified to be a photograph, the output of the dither process section 4 is supplied to the output terminal 9, and when the input is identified to be a screen halftone, the output of the dither process section 3 is supplied to the output terminal 9.

A detailed description on the image signal power detection section 6 and the image identification section 7 is set forth below.

An explanation is provided respectively with respect to the features of the power spectra in the main scanning direction and the subscanning direction of a flat part, an edge part and a periodic pattern part of a character, a photograph and a screen halftone. The flat part means a part where the density change is small; the edge part means a part where the density change is large; the periodic pattern part means a part where similar patterns are periodically repeated. The periodic pattern part often appears in character images.

(1) Characters

Characters have features in the edge part and the periodic pattern part in either the main scanning direction or the subscanning direction. The frequency range of an image signal of a character is examined by Fourier transformation and it is found that the signal has a large power distribution in a wide range only in a direction of either the main scanning direction or the subscanning direction.

FIG. 3A shows a spatial frequency distribution in the main scanning direction of a flat part of a character. In FIG. 3A, f1 denotes a pitch frequency (fundamental frequency) of mesh points corresponding to the number of lines of a screen halftone; f2 is lower than f1 and denotes a frequency at which the power of the screen halftone becomes minimum; f3 denotes the maximum picture frequency of the image signal which is determined by the reading resolution when the image signal is digitized.

As mentioned above, the features in the power spectrum of a screen halftone appear at frequencies f1, f2 and f3. It is a point of the present invention to identify a character, a photograph or a screen halftone by taking advantage of the fact that each image signal of a character, a photograph or a screen halftone has different features at f1, f2 and f3 in the power spectrum.

The expressions tm(1), tm(2) and tm(3) denote threshold values of the power pm(1), pm(2) and pm(3) at f1, f2 and f3. The expressions dm(1), dm(2) and dm(3) denote criterion values, and when $tm(i) < pm(i)$, $dm(i) = 1$, and when $tm(i) \geq pm(i)$, $dm(i) = 0$. As shown in FIG. 3A, $tm(i) \geq pm(i)$, so that $dm(1) = 0$, $dm(2) = 0$ and $dm(3) = 0$. This means that the power spectrum appears only in the vicinity of zero spatial frequency.

FIG. 3B shows the spatial frequency distribution of a flat part of a character in the subscanning direction. The expressions ts(1), ts(2) and ts(3) denote threshold values of the power ps(1), ps(2) and ps(3) at f1, f2 and f3. The expressions ds(1), ds(2) and ds(3) denote criterion values, and when $ps(i) > ts(i)$, $ds(i) = 1$, and when $ps(i) \leq ts(i)$, $ds(i) = 0$.

As shown in FIG. 3B in the case of the subscanning direction, similar to FIG. 3A, the power spectrum appears only in the vicinity of zero spatial frequency.

Figure 4B:
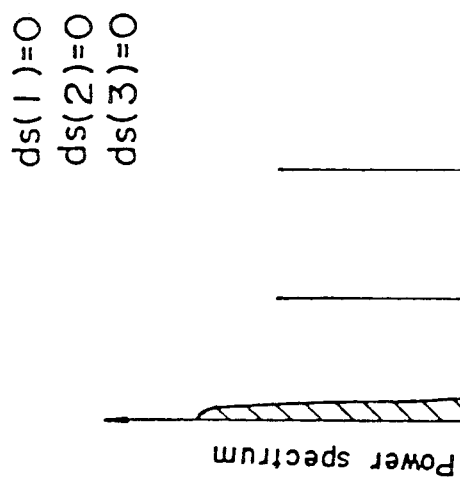
FIG. 4B is a spatial frequency distribution chart in the subscanning direction of a character having an edge in the main scanning direction.
Figure 4A:
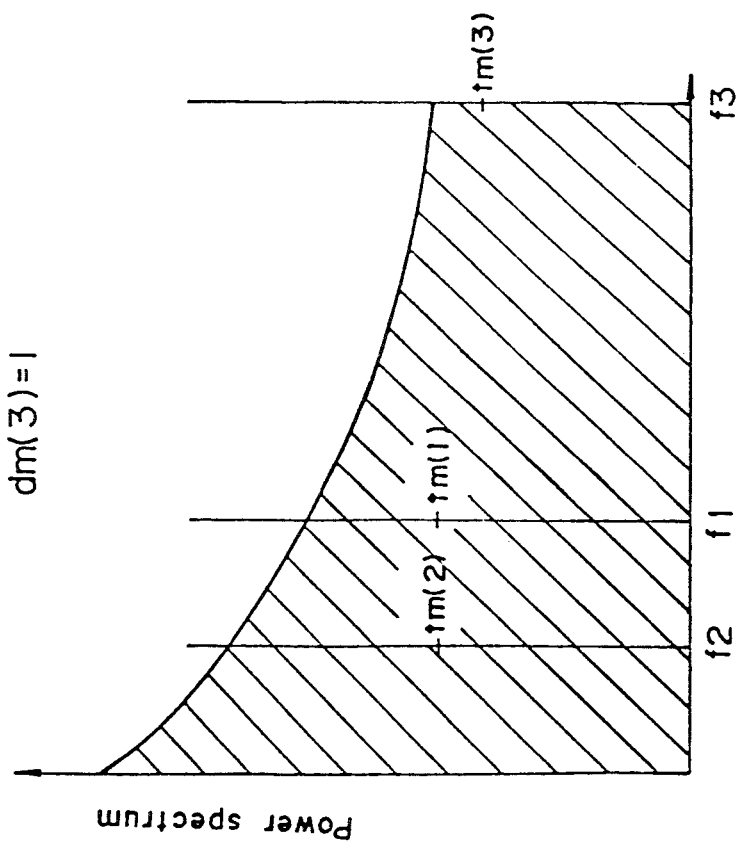
FIG. 4A is a spatial frequency distribution chart in the main scanning direction of a character having an edge in the main scanning direction.

FIG. 4A shows the spatial frequency distribution in the main scanning direction of a character having an edge in the main scanning direction. The power spectrum shows large values in the range of frequencies from 0 to f3.

FIG. 4B shows the spatial frequency distribution in the subscanning direction of a character having an edge in the main scanning direction. The power spectrum appears only in the vicinity of zero frequency.

Figure 6A:
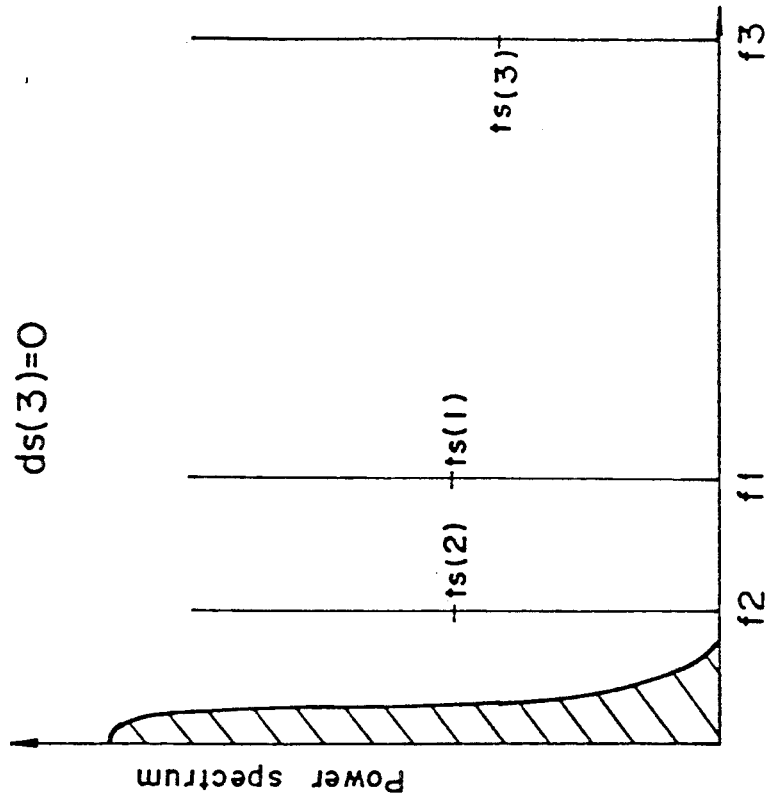
FIG. 6A is a spatial frequency distribution chart in the main scanning direction of a character having a periodic pattern in the main scanning direction.

FIG. 5A shows the spatial frequency distribution in the main scanning direction of a character having an edge in the subscanning direction, and FIG. 5B shows the spatial frequency distribution in the subscanning direction of a character having an edge in the subscanning direction. FIG. 4A and FIG. 5B, and FIG. 4B and FIG. 5A have respectively similar power spectra. FIG. 6A shows a spatial frequency distribution in the main scanning direction of a character having a periodic pattern in the main scanning direction. It has a peak between the frequencies in the vicinity of zero and f1, and another peak between f1 and f3, and has a minimum point in the vicinity of f2.

Figure 6B:
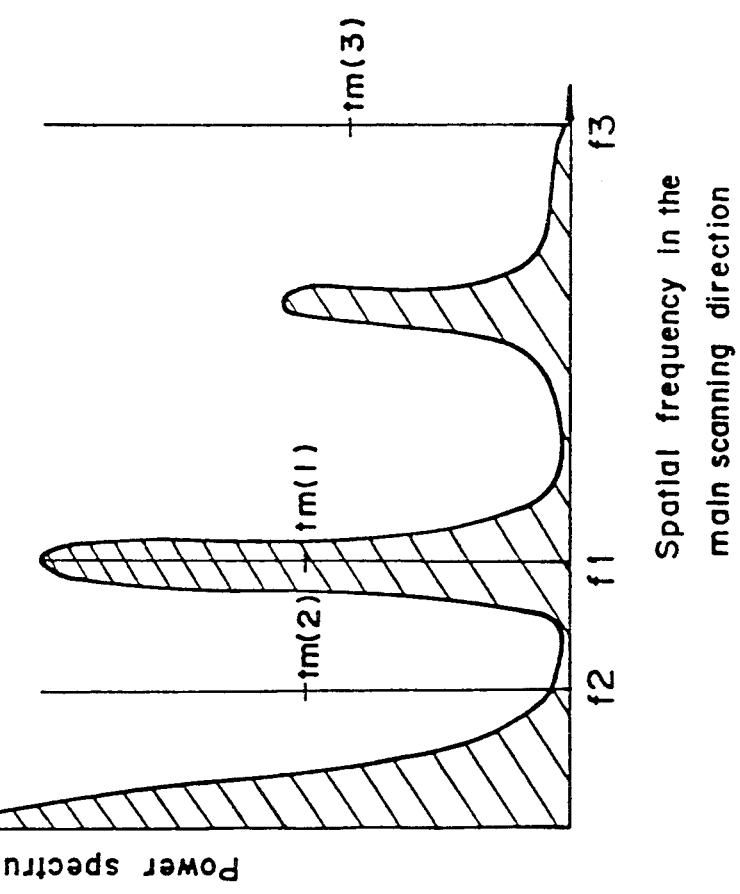
FIG. 6B is a spatial frequency distribution chart in the subscanning direction of a character having a periodic pattern in the main scanning direction.

FIG. 6B shows a spatial frequency distribution in the subscanning direction of a character having a periodic pattern in the main scanning direction. The power spectrum is found only in the vicinity of zero frequency.

Figure 7A:
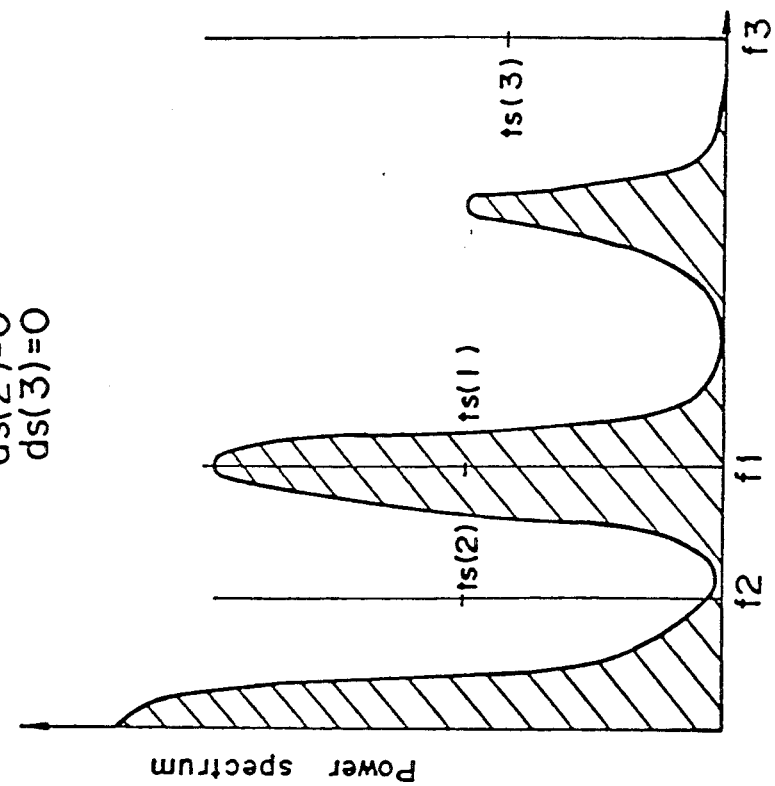
FIG. 7A is a spatial frequency distribution chart in the main scanning direction of a character having a periodic pattern in the subscanning direction.
Figure 7B:
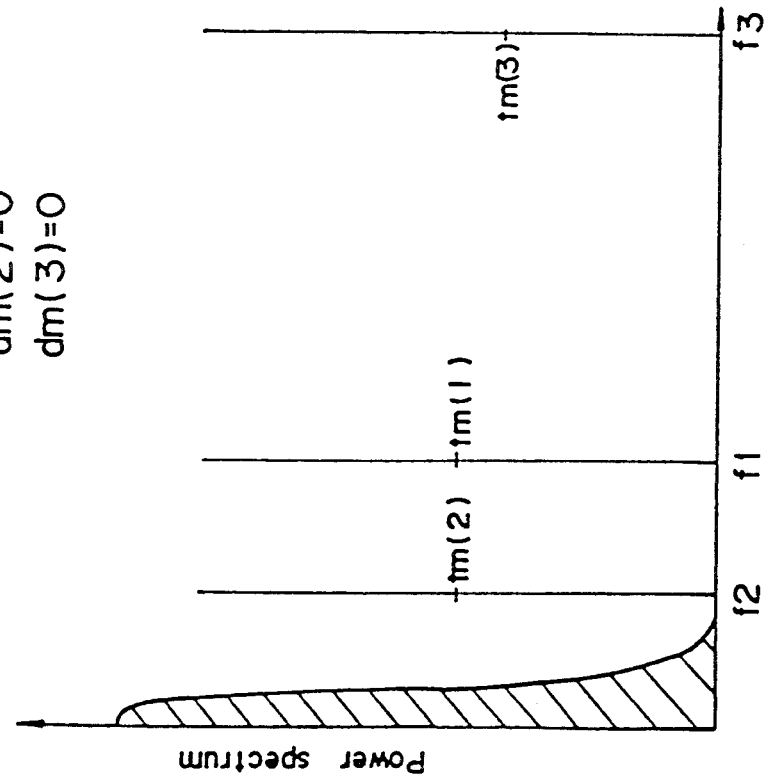
FIG. 7B is a spatial frequency distribution chart in the subscanning direction of a character having a periodic pattern in the subscanning direction.

FIG. 7A shows a spatial frequency distribution in the main scanning direction of a character having a periodic pattern in the subscanning direction, and FIG. 7B shows a spatial distribution in the subscanning direction of a character having a periodic pattern in the subscanning direction. FIG. 6A and FIG. 7B, and FIG. 6B and FIG. 7A have power spectra of similar patterns.

(2) Photograph

The feature of a photograph lies in that the change of density is less drastic than that of a character. When it is examined from the point of view of the frequency range, the power in the power spectrum in the higher frequency range is found to be small.

Figure 8A:
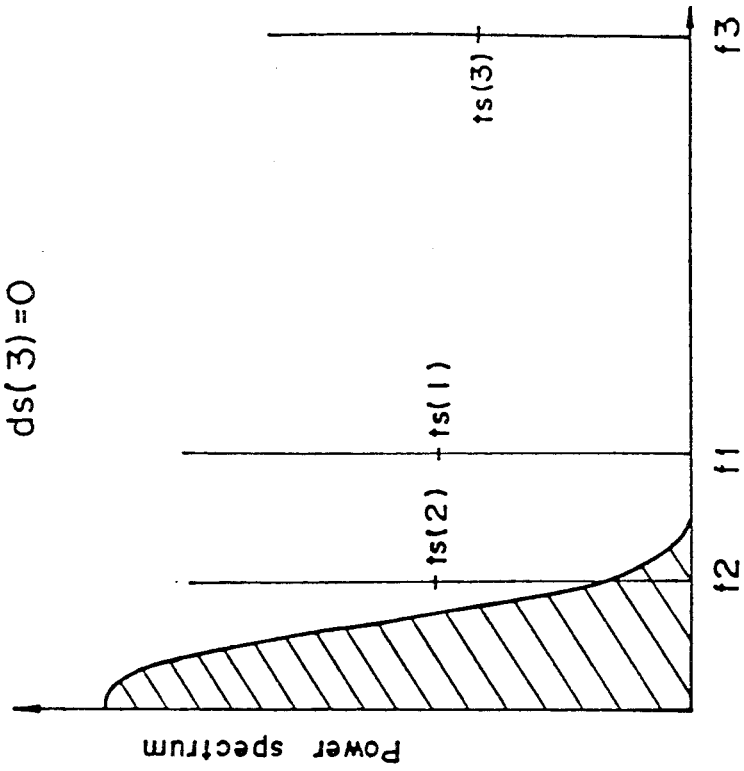
FIG. 8A is a spatial frequency distribution chart in the main scanning direction of a flat part of a photograph.

FIG. 8A shows a spatial frequency distribution in the main scanning direction of a flat part of a photograph. In the spectrum power is concentrated between the frequency 0 and f2.

Figure 8B:
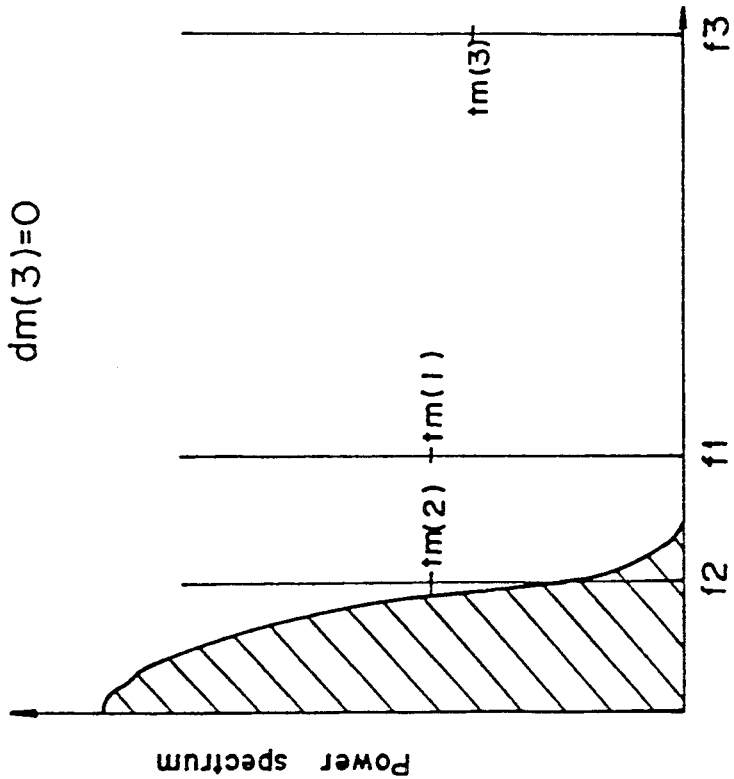
FIG. 8B is a spatial frequency distribution chart in the subscanning direction of a flat part of a photograph.

FIG. 8B shows a spatial frequency distribution in the subscanning direction of a flat part of a photograph. The state of the spatial frequency distribution is similar to that of FIG. 8A.

FIG. 9A shows a spatial frequency distribution in the main scanning direction of a photograph having an edge in the main scanning direction. The power spectrum shows a maximum value at frequency 0, and the value decreases as the frequency increases and becomes 0 in the vicinity of f3.

FIG. 9B shows a spatial frequency distribution in the subscanning direction of a photograph having an edge in the main scanning direction. In the spectrum, power is concentrated between the frequency 0 and f2.

Figure 10A:
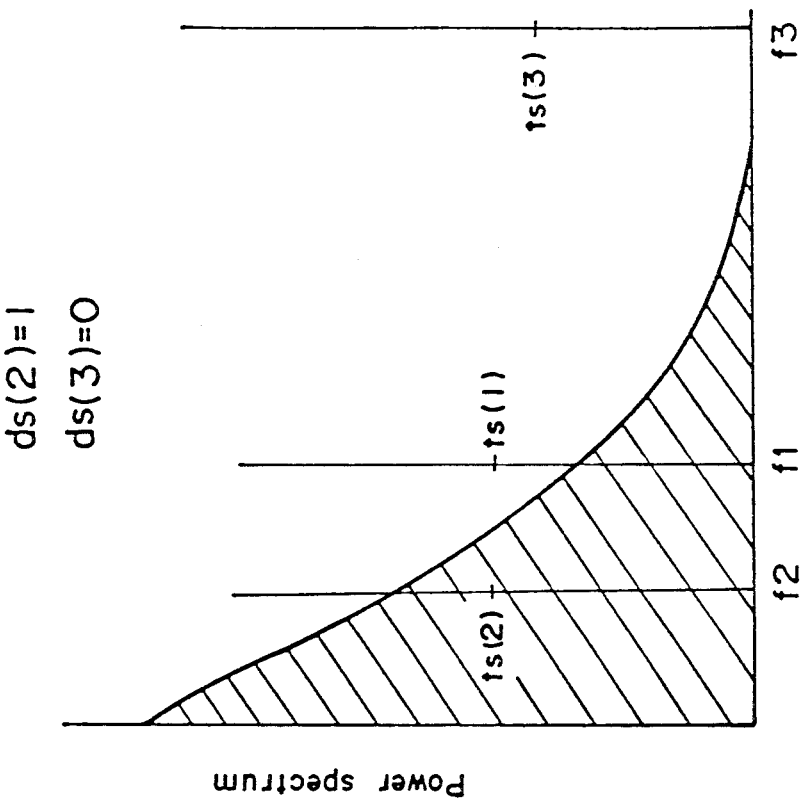
FIG. 10A is a spatial frequency distribution chart in the main scanning direction of a photograph having an edge in the subscanning direction.

FIG. 10A shows a spatial frequency distribution in the main scanning direction of a photograph having an edge in the subscanning direction.

Figure 10B:
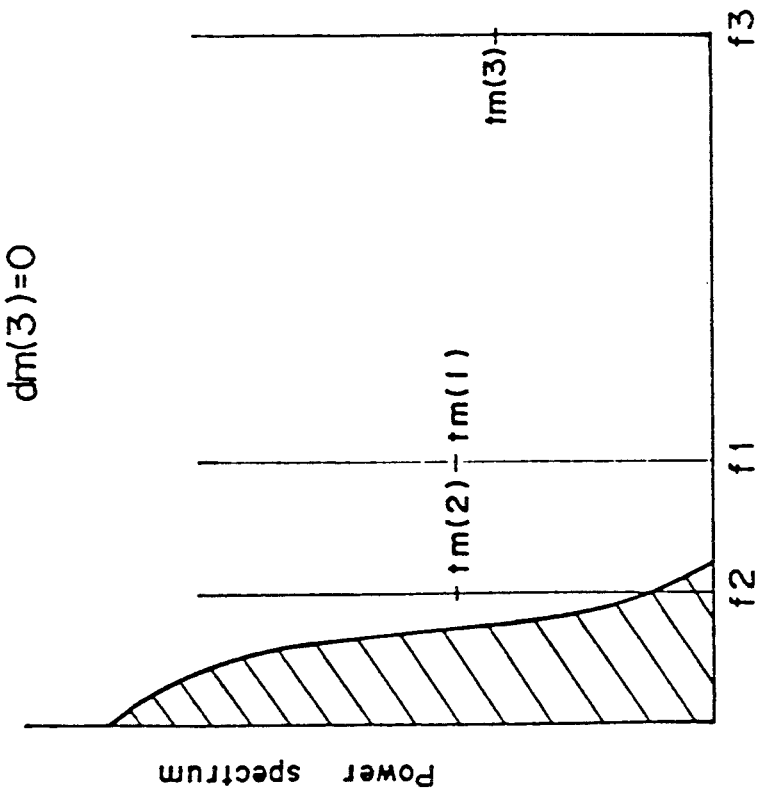
FIG. 10B is a spatial frequency distribution chart in the subscanning direction of a photograph having an edge in the subscanning direction.

FIG. 10B shows a spatial frequency distribution in the subscanning direction of a photograph having an edge in the subscanning direction.

FIG. 9A and FIG. 10B, and FIG. 9B and FIG. 10A have spatial frequency distributions of similar patterns.

(3) Screen halftone

A screen halftone in which mesh points are disposed being inclined at an angle of 45 (screen angle 45) is taken up as an object. A screen halftone is the one in which the variation of the density of a photograph is converted to the sizes of mesh points. When a screen halftone is examined from the view point of frequency range, the peaks in the power spectrum are found at the mesh point pitch frequency corresponding to the number of mesh point lines and at its higher harmonic frequencies in the main scanning direction and subscanning direction.

FIG. 11A shows a spatial frequency distribution in the main scanning direction of a flat part of a screen halftone. In the power spectrum, there are peaks at frequencies 0 and f1, and between f1 and f3, and minimum points in the vicinity of f2 and f3.

FIG. 11B shows a spatial frequency distribution in the subscanning direction of a flat part of a screen halftone. The spatial frequency distribution is similar to that shown in FIG. 11A.

Figure 12A:
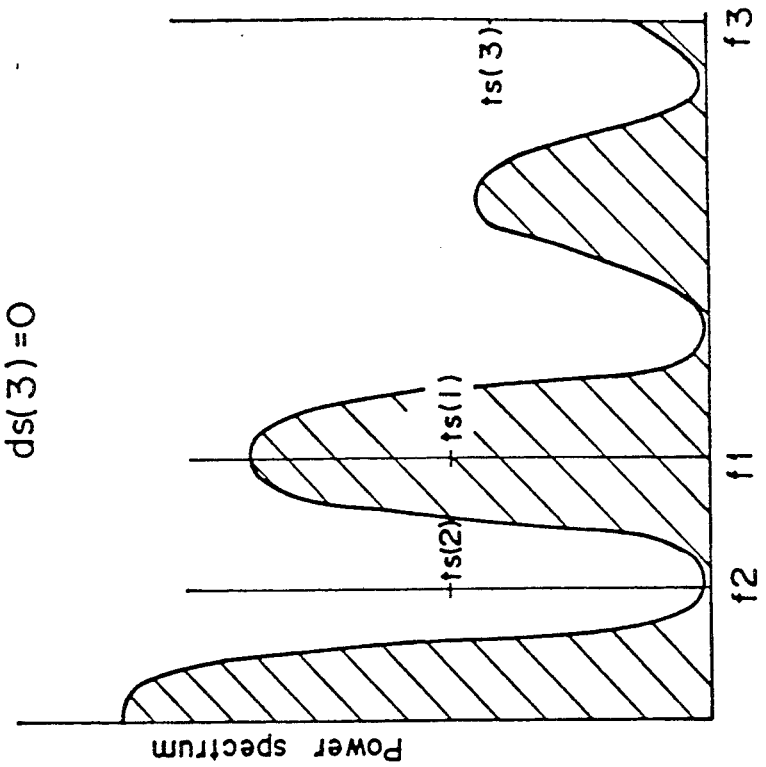
FIG. 12A is a spatial frequency distribution chart in the main scanning direction of a screen halftone having an edge in the main scanning direction.

FIG. 12A shows a spatial frequency distribution in the main scanning direction of a screen halftone having an edge in the main scanning direction. There are peaks at frequencies 0 and f1, and between f1 and f3, and minimum points in the vicinity of f2 and f3 in the power spectrum. Large values are found ranging from frequency 0 to f3 in the power spectrum.

Figure 12B:
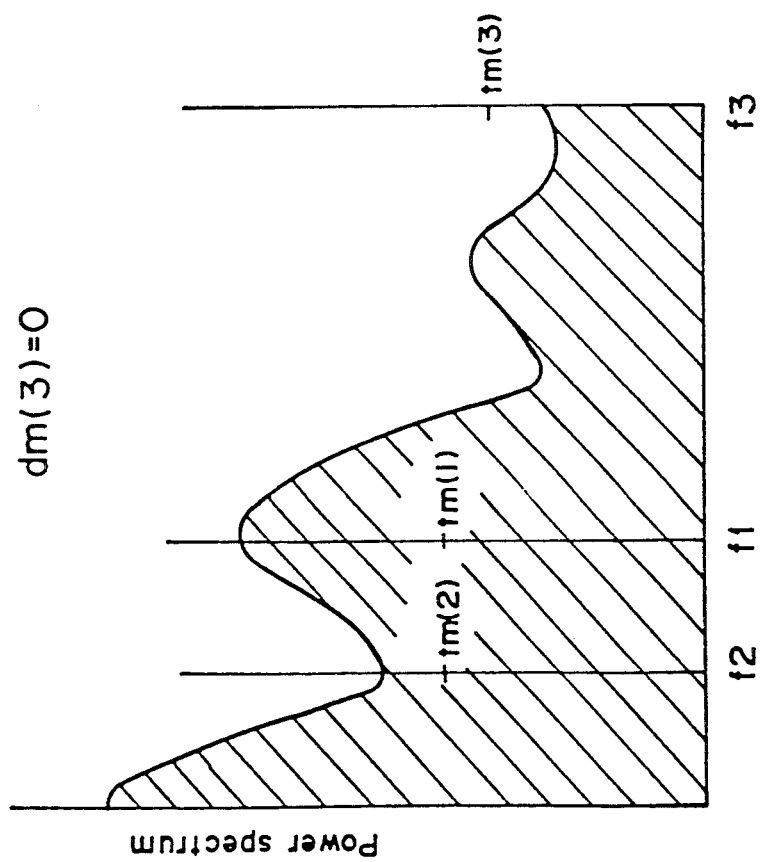
FIG. 12B is a spatial frequency distribution chart in the subscanning direction of a screen halftone having an edge in the main scanning direction.

FIG. 12B shows a spatial frequency distribution in the subscanning direction of a screen halftone having an edge in the main scanning direction. The frequency distribution is similar to those shown in FIG. 11A and FIG. 11B.

Figure 13A:
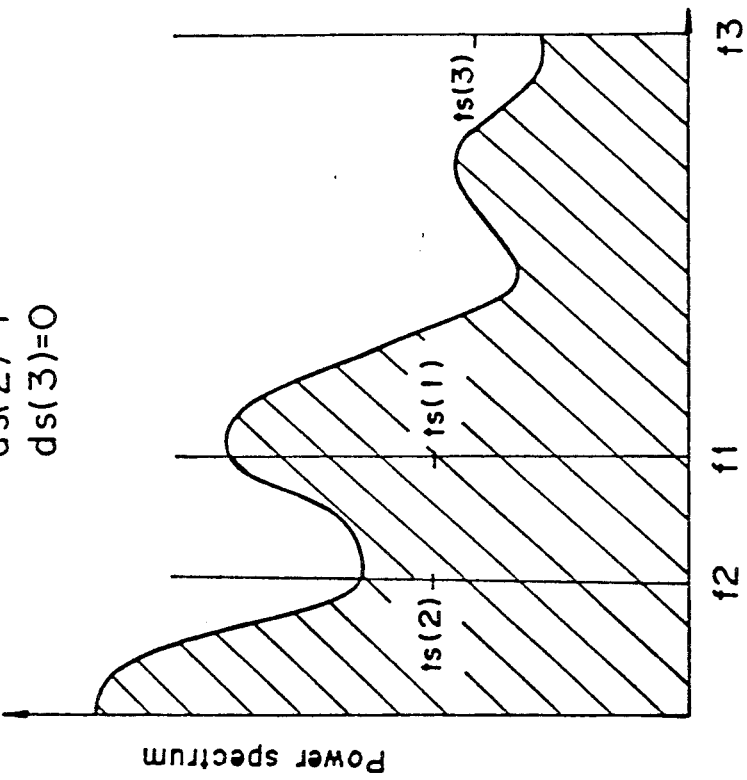
FIG. 13A is a spatial frequency distribution chart in the main scanning direction of a screen halftone having an edge in the subscanning direction.

FIG. 13A shows a spatial frequency distribution in the main scanning direction of a screen halftone having an edge in the subscanning direction.

Figure 13B:
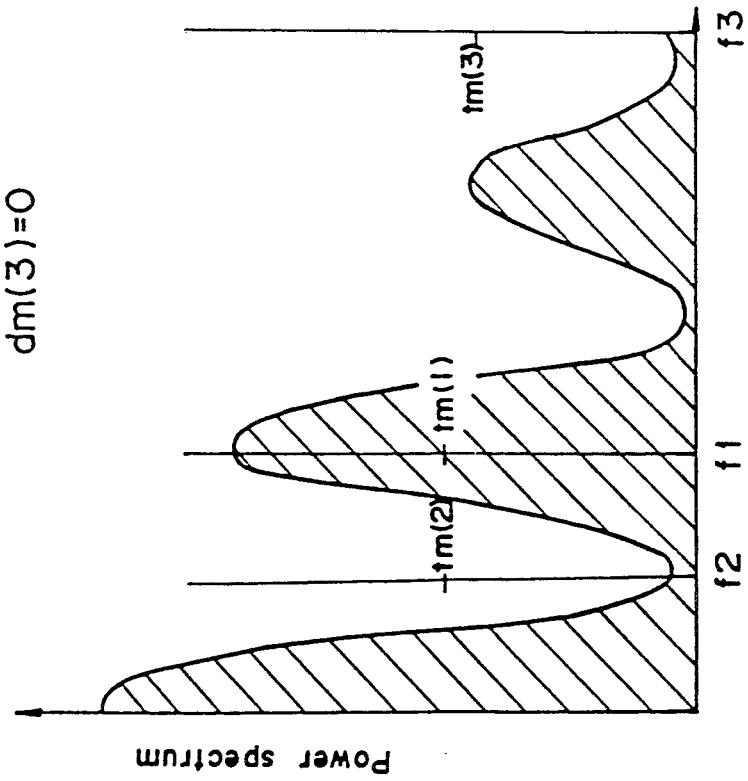
FIG. 13B is a spatial frequency distribution chart in the subscanning direction of a screen halftone having an edge in the subscanning direction.

FIG. 13B shows a spatial frequency distribution in the subscanning direction of a screen halftone having an edge in the subscanning direction. The power spectra are similar to each other in FIG. 12A and FIG. 13B, and in FIG. 12B and FIG. 13A.

As described in the above, each of these power spectrum frequency characteristics of a character, a photograph and a screen halftone has its inherent features.

As shown in FIG. 2, the image signal power detection section 6 detects power spectrum vectors $\overline{pm}$ (pm(1), pm(2) - - - pm(n)) comprising the power pm(i) (i = 1 to n) at plural fixed frequencies f1 to fn in the main scanning direction, and power spectrum vectors $\overline{ps}$ (ps(1), ps(2) - - - ps(n)) comprising the power ps(i) (i = 1 to n) at frequencies f1 to fn in the subscanning direction. The image identification section 7 identifies an input image signal to be one of the following parts by making the reference vector generating section 9 generate a reference vector based on FIG. 3A to FIG. 13B, and by performing pattern matching between the reference vector and $\overline{pm}$ and $\overline{ps}$ in the pattern matching section:

a. a flat part of a character,
b. an edge part in the main scanning direction of a character,
c. an edge part in the subscanning direction of a character,
d. a periodic pattern part in the main scanning direction of a character,
e. a periodic pattern part in the subscanning direction of a character,
f. a flat part of a photograph,
g. an edge part in the main scanning direction of a photograph,
h. an edge part in the subscanning direction of a photograph,
i. a flat part of a screen halftone,
j. an edge part in the main scanning direction of a screen halftone,
k. an edge part in the subscanning direction of a screen halftone.

A proper image process for an identified image as mentioned above is explained below.

The principle of image processes is as shown below: for a character a binarization process is applied; for a photograph a dither process is applied; for a screen halftone a dither process is applied after a mesh point structure is removed by a low-pass filter.

The processes are executed based on FIG. 3A to FIG. 13B as described in the following.

The power spectrum of a character flat part "a" (FIG. 3A and FIG. 3B) is different from the power spectra of other parts "b" to "e" of a character (FIG. 4A to FIG. 7B) and it is rather analogous to the power spectra of "f", "g" and "h" of a photograph (FIG. 8A to FIG. 10B). A dither process is therefore preferable for the part "a". The power in the power spectrum of the part "a" is distributed in the low frequency range, so that it is also preferable to perform a dither process after the low-pass filter process.

The power in the power spectrum of a photograph flat part "f" is distributed in the low frequency range, so that a simple dither process or a dither process after the low-pass filter process is the proper way of processing.

The edge parts "j" and "k" are blurred by a low-pass-filter process, so that a simple dither process is desirable.

The description above is summarized in the following:

(1) the cases in which a binarization process is desirable are

"b", "c", "d" and "e", (2) the cases in which a dither process is desirable are

"a", "f", "g", "h", "j" and "k", (3) the cases in which a dither process after a low-pass-filter process is desirable are, "a", "f", and "i".

Figure 14:
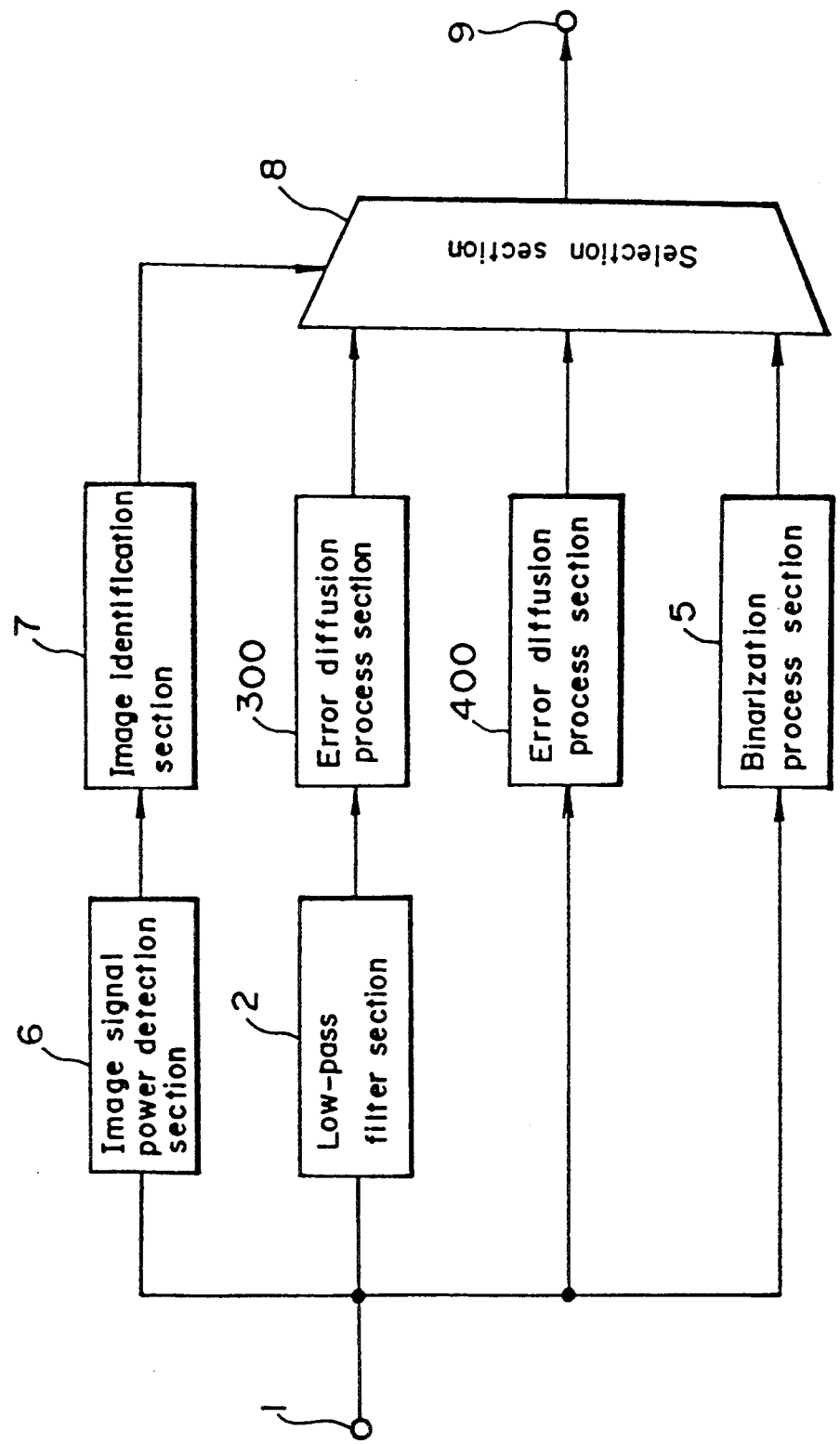
FIG. 14 is a block diagram of a second embodiment.

FIG. 14 shows a block diagram of a second embodiment. The difference between the second embodiment and the first embodiment shown in FIG. 1 is that the dither process sections 3 and 4 of the first embodiment are substituted with error diffusion sections 300 and 400.

An error diffusion process is a generally known technique in which the mean density of an input image is made to be equal to that of an output image by reflecting errors produced when the picture elements surrounding a given picture element are binarized to the binarization of the picture element.

This process is effective for preventing the occurrence of moire stripes. This is a quasi-tone reproduction process similar to a dither process, and so it can be replaced with a dither process.

Figure 15:
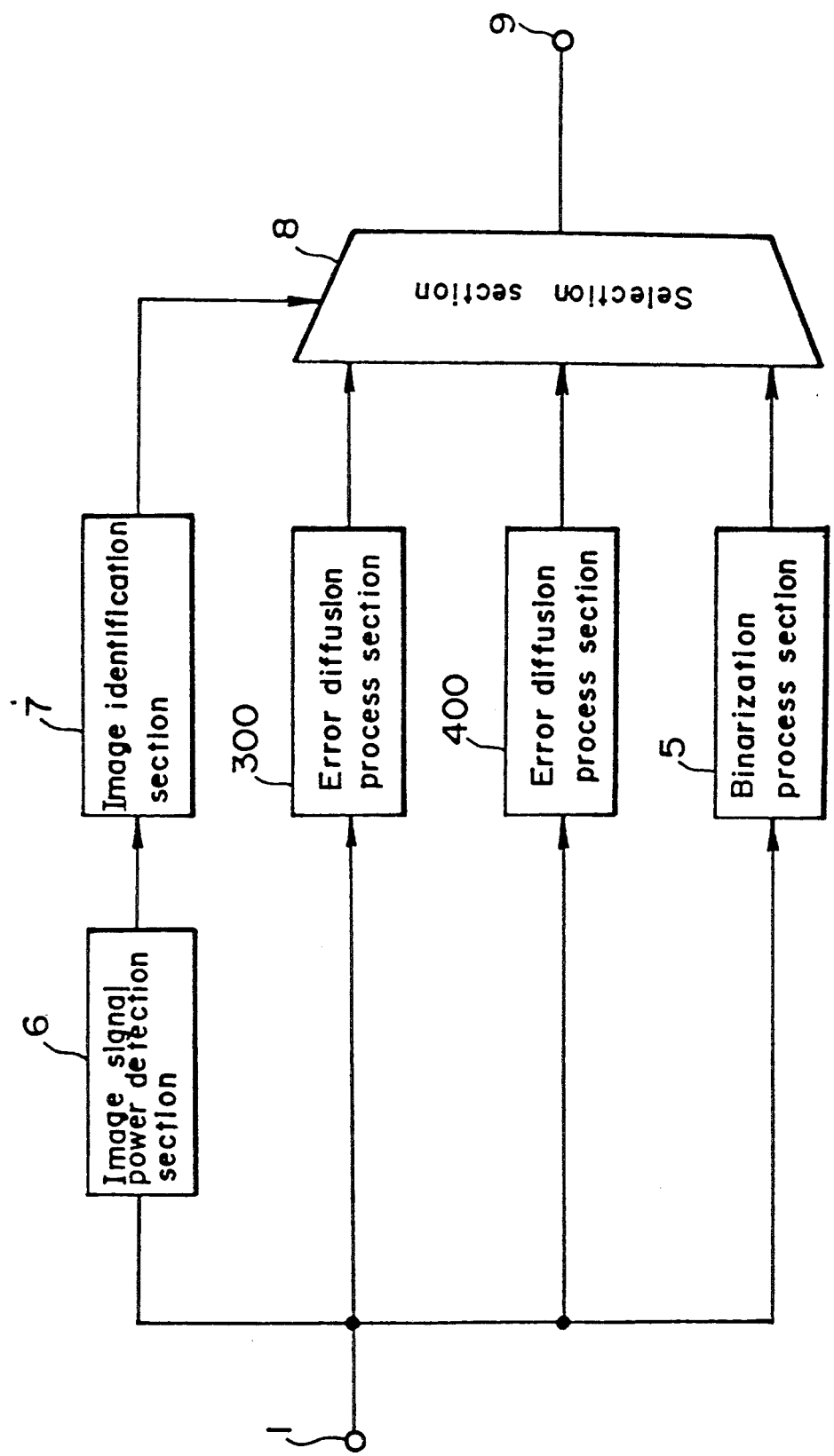
FIG. 15 is a block diagram of a third embodiment.

FIG. 15 is a block diagram showing a third embodiment. The difference between the third embodiment and the second embodiment shown in FIG. 14 is that the low-pass filter section 2 of the second embodiment is removed. The error diffusion process has, as mentioned above, a merit in that moire stripes do not occur easily in comparison with the case of the dither process. There is therefore little necessity of preprocessing a low-pass filter process for a screen halftone, making it possible to eliminate the low-pass filter section 2.

Figure 16:
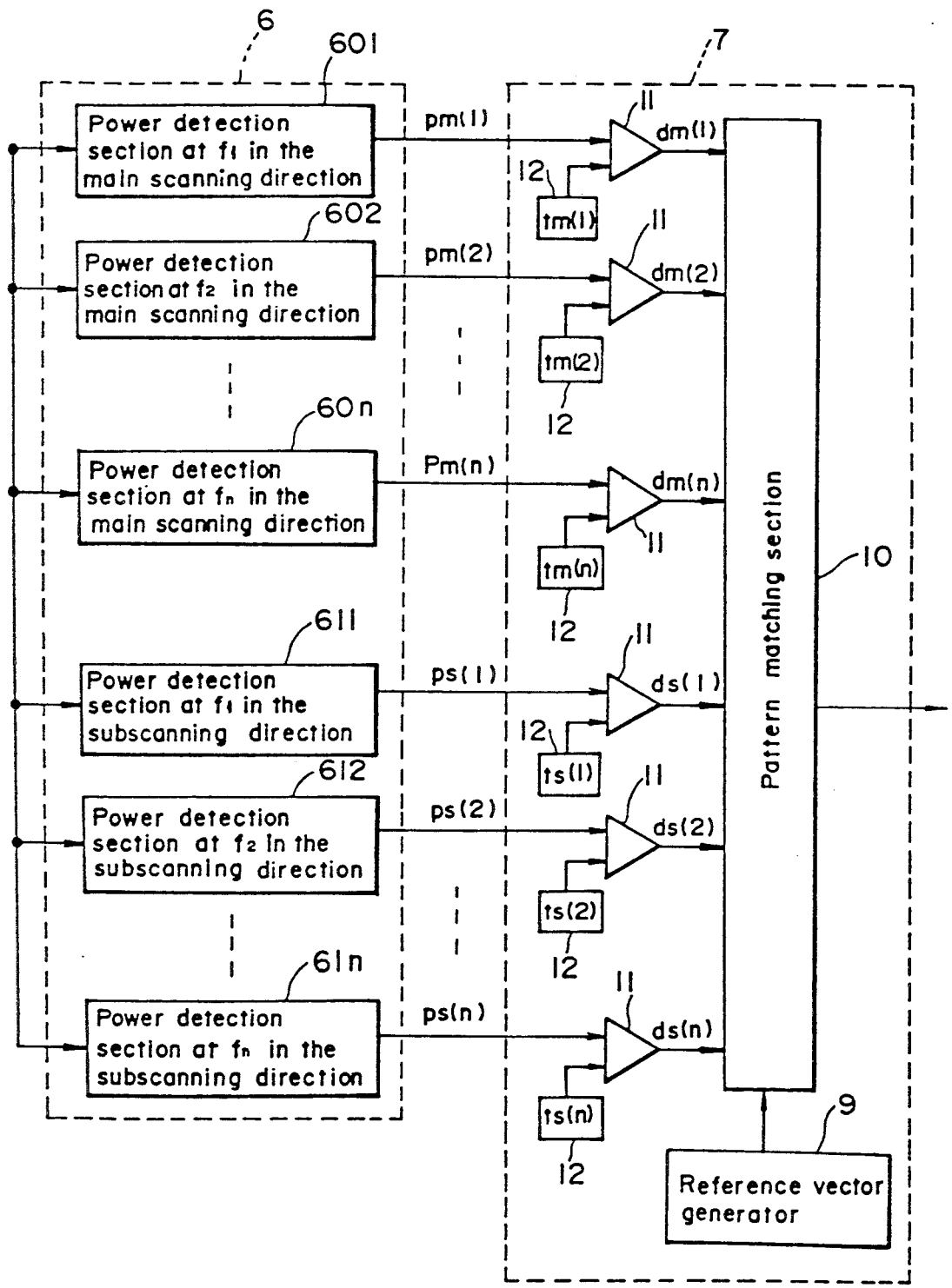
FIG. 16 is a detailed drawing of an image signal power detection section and an image identification section in a fourth embodiment.

A fourth embodiment is explained referring to FIG. 16. FIG. 16 shows a configuration in which a comparator 11 is added to the image identification section 7 shown in FIG. 2.

The comparator 11 outputs to the patterns matching section 10 the value of a criterion dm(i) calculated by comparing a power pm(i) at a fixed frequency fi in the main scanning direction and a threshold value tm(i) generated by a threshold value generator 12, and the value of a criterion ds(i) calculated by comparing a power ps(i) at a fixed frequency fi in the subscanning direction and a threshold value ts(i) generated by a threshold value generator 12. Thus the identification function of the pattern matching section 10 is simplified in comparison to the first embodiment.

As described in the first embodiment, a power spectrum vector in the main scanning direction $\overline{pm}$ (pm(1), pm2), - - - pm(n)) and a power spectrum vector in the subscanning direction $\overline{ps}$ (ps(1), ps(2), - - - ps(n)) are detected by the image signal power detection section 6. The image identification section 7 outputs the criterion value vectors $\overline{dm}$ and $\overline{ds}$ in accordance with the comparison of $\overline{pm}$ and $\overline{ps}$ and the threshold value vectors $\overline{tm}$ (tm(1), tm(2), - - - tm(n)) and $\overline{ts}$ (ts(1), ts(2), - - - ts(n)) which are set beforehand.

When pm(k)>tm(k), dm(k)=1;
when pm(k)≦tm(k), dm(k)=0;
when ps(k)>ts(k), ds(k)=1;
when ps(k)≦ts(k), ds(k)=0.

The identification of an input image is effected by comparing $\overline{dm}$ and $\overline{ds}$ with the reference vectors obtained from FIG. 3A to FIG. 13B in the pattern matching section 10.

Figure 17:
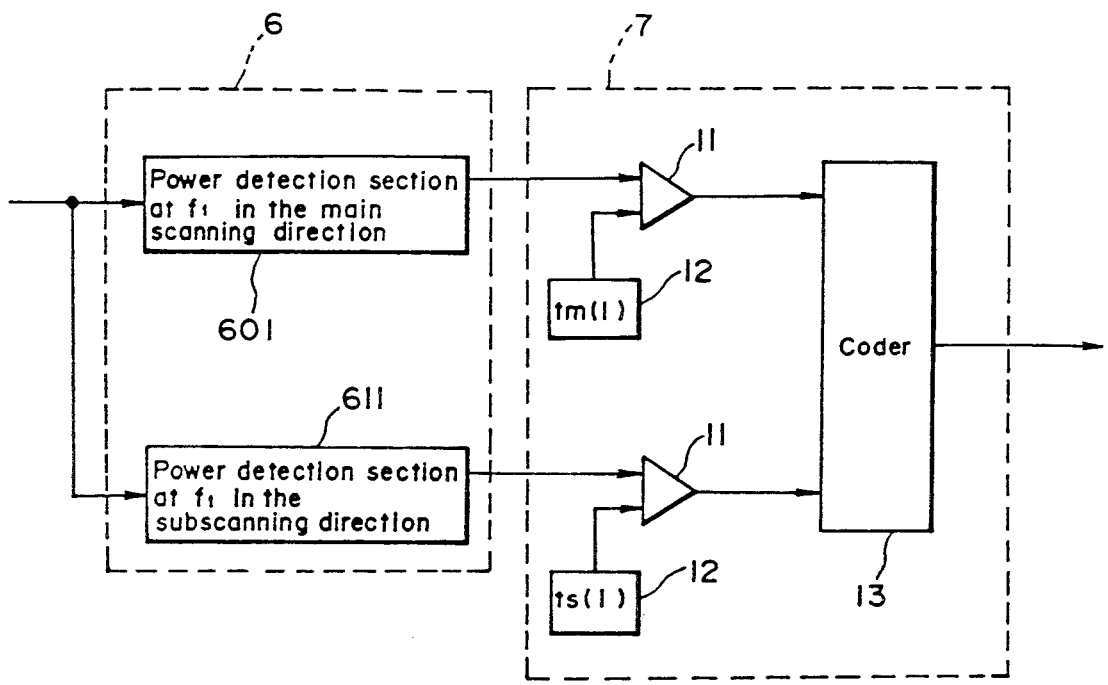
FIG. 17 is a detailed drawing of an image signal power detection section and an image identification section in a fifth embodiment.

A fifth embodiment is explained referring to FIG. 17. FIG. 17 shows a simplified configuration of the image signal power detection section 6 and the image identification section 7 shown in FIG. 16, and the above-mentioned image signal power detection section 6 and the image identification section 7 are constituted with only power detection sections 601 and 611 at frequency f1 in the main scanning direction and the subscanning direction. A coder 13 corresponds to the reference vector generator 9 and the pattern matching section 10 shown in FIG. 16, but its configuration is made simpler than those of the above sections.

The frequency characteristics of a character, a photograph and a screen halftone are much different from one another as explained in FIG. 3A to FIG. 13B. The power values pm(1) and ps(1) in the main scanning direction and the subscanning direction at a basic frequency f1 of a screen halftone are especially worthy of attention as shown below.

|  | pm(1) | ps(1) |
|---|---|---|
| (1) Character | | |
| Flat part | small | small |
| Edge part in the main scanning direction | large | small |
| Edge part in the subscanning direction | small | large |
| Periodic pattern section in the main scanning direction | large | small |
| Periodic pattern section in the subscanning direction | small | large |
| (2) Photograph | | |
| Flat part | small | small |
| Edge part in the main scanning direction | small | small |
| Edge part in the subscanning direction | small | small |
| (3) Screen halftone | | |
| Flat part | large | large |
| Edge part in the main scanning direction | large | large |
| Edge part in the subscanning direction | large | large |

When criterion value vectors dm and ds described in the fourth embodiment are used, the frequency is limited only to f1, so that criterion values are expressed using dm(1) and ds(1).

A proper process method for each type of input images is shown below when using dm(1) and ds(1) as parameters:

(1) when (dm(1), ds(1)) =(0, 0),
the input image is identified to be a flat part of a photograph or a character, and it is dither-processed;

(2) when (dm(1), ds(1))=(0, 1),
the input image is identified to be an edge part or a periodic pattern part of a character in the subscanning direction, and it is binarized;

(3) when (dm(1), ds(1))=(1, 0),
the input image is identified to be an edge part or a periodic pattern part of a character in the main scanning direction, and it is binarized;

(4) when (dm(1), ds(1))=(1, 1),
the input image is identified to be a screen halftone, ad it is dither-processed after a low-pass-filter process.

Figure 18:
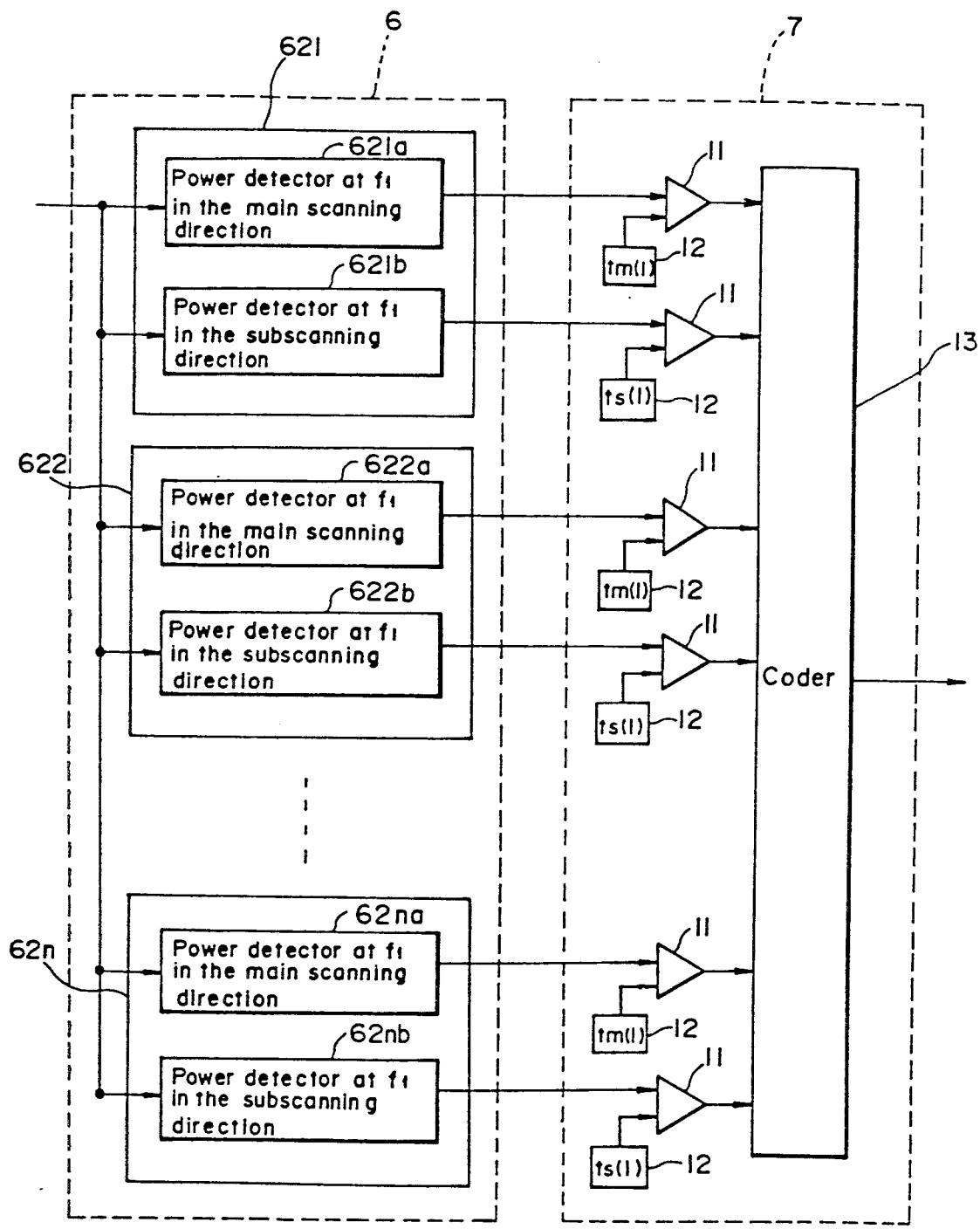
FIG. 18 is a detailed drawing of an image signal power detection section and an image identification section in a sixth embodiment.

A sixth embodiment is explained referring to FIG. 18. The image signal power detection section 6 in the fifth embodiment shown in FIG. 17 detects the image signal power at the fundamental frequency f1 of a screen halftone. The fundamental frequency f1 of a screen halftone differs depending on the number of lines, if the power of a plurality of screen halftones having a different number of lines is detected at a single fundamental frequency f1, the detection accuracy is degraded. The number of lines generally used are, for example, 85 lines (85 dots/inch), 133 lines, 150 lines and 200 lines.

FIG. 18 shows a device which has an image signal detection section 6 comprising power detectors corresponding to each number of these lines. A power detector 621 for 85 lines comprises a power detector 621a in the main scanning direction and a power detector 621b in the subscanning direction at a fundamental frequency f1 corresponding to 85 lines of a screen halftone.

A power detector 622 for 133 lines comprises a power detector 622a in the main scanning direction and a power detector 622b in the subscanning direction at a fundamental frequency f1 corresponding to 133 lines of a screen halftone.

When a screen halftone of 85 lines is input to the image signal power detection section 6, the output of the power detector 621 for 85 lines is output to the image identification section 7, and then a similar process to that shown in the fifth embodiment is executed.

Figure 19:
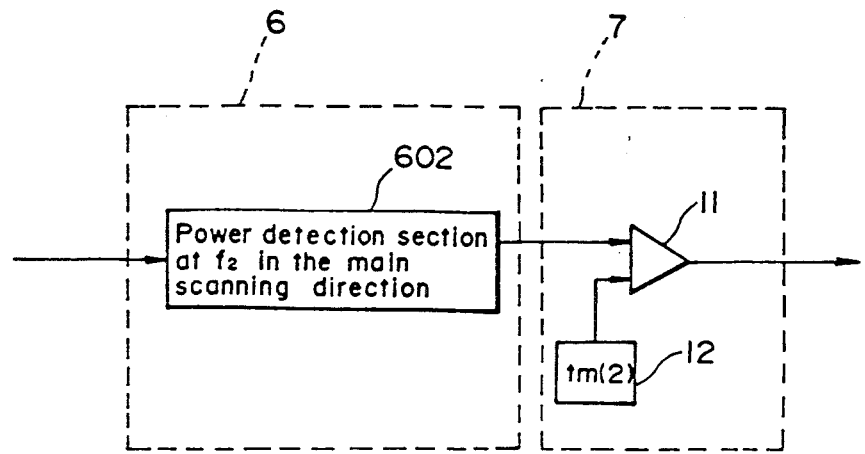
FIG. 19 is a detailed drawing of an image signal power detection section and an image identification section in a seventh embodiment.

A seventh embodiment is explained referring to FIG. 19. In any image of a character, a photograph or a screen halftone, a frequency characteristic in a flat part and that in an edge part have remarkable features which different from each other. The power pm(2) at frequency f2 especially in the main scanning direction has a feature as shown below.

|  | pm(2) |
|---|---|
| (1) Character | |
| Flat part | small |
| Edge part in the main scanning direction | large |
| (2) Photograph | |
| Flat part | small |
| Edge part in the main scanning direction | large |
| (3) Screen halftone | |
| Flat part | small |
| Edge part in the main scanning direction | large |

A proper process for each type of input images is described below using the criterion value dm(2) as a parameter which is described in the fourth embodiment:

(1) when dm(2)=0,
the input image is identified to be a flat part of a character, a photograph or a screen halftone, and it is dither-processed after a low-pass-filter process;

(2) when dm(2)=1,
the input image is identified to be an edge part in the main scanning direction, and it is binarized.

In the case of the present embodiment, the detection of only the power in the main scanning direction at frequency f2 is needed, so that the configuration of the image signal power detection section 6 is much simplified and includes only the f2 power detector 602, and the configuration of the image identification section 7 is also much simplified and includes only a pair of a comparator 11 and a threshold value generator 12.

In the case of a manuscript of a character, a photograph or a screen halftone which has a lot of flat parts and edge parts in the subscanning direction, the detection of only the power ps(2) at f2 in the subscanning direction is sufficient.

Figure 20:
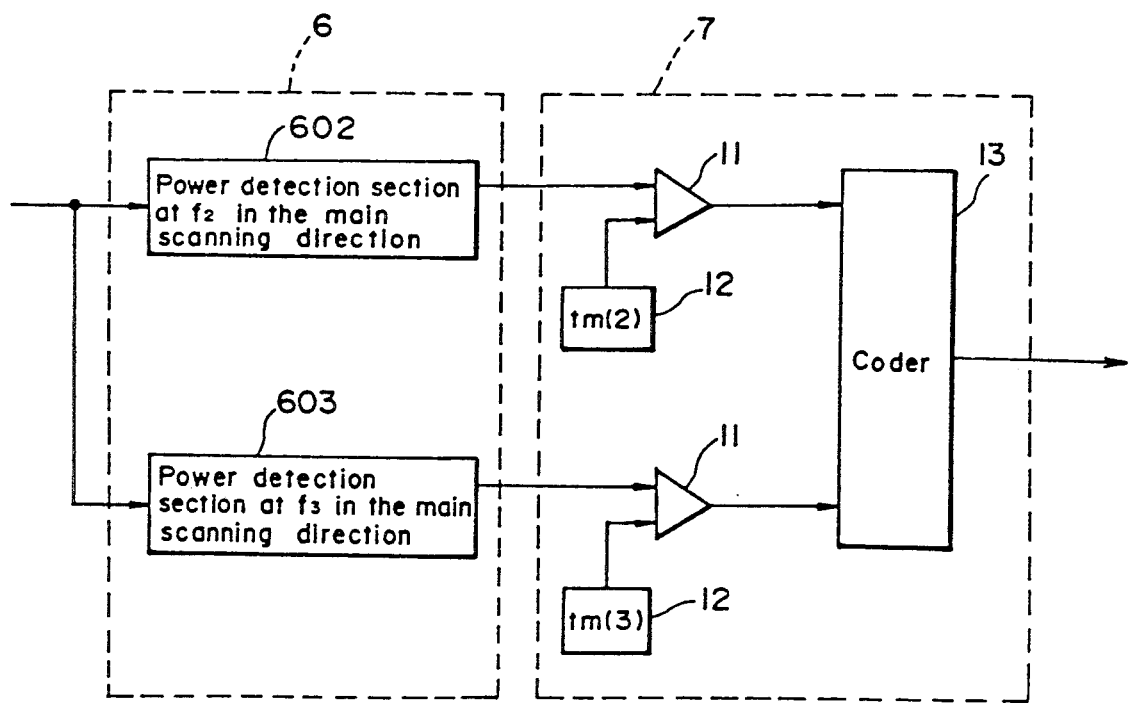
FIG. 20 is a detailed drawing of an image signal power detection section and an image identification section in an eighth embodiment.

An eighth embodiment is explained referring to FIG. 20. In the seventh embodiment, the edge part of a character cannot be discriminated from the edge part of a halftone image (a photograph and a screen halftone). Because of this, binarization process is done for the edge part of a halftone image, while a dither process is originally suitable for the part. In the present embodiment, the edge part of a character and the edge part of a halftone image are discriminated from each other as shown below, and only the dither process is effected for the edge part of a halftone image.

The power pm(2) at frequency f2 in the main scanning direction and the power pm(3) at frequency f3 in the main scanning direction have the following features:

|  | pm(2) | pm(3) |
|---|---|---|
| (1) Character | | |
| Flat part | small | small |
| Edge part in the main scanning direction | large | large |
| (2) Photograph | | |
| Flat part | small | small |
| Edge part in the main scanning direction | large | small |
| (3) Screen halftone | | |
| Flat part | small | small |
| Edge part in the main scanning direction | large | small |

A proper process for each type of an input image using criterion values dm(2) and dm(3) as parameters explained in the fourth embodiment is shown below:

(1) when (dm(2), dm(3))=(0, 0), the input image is identified to be a flat part of a character, a photograph or a screen halftone, and it is dither-processed after a low-pass-filter process;

(2) when (dm(2), dm(3))=(1, 0) the input image is identified to be an edge part in the main direction of a photograph or a screen halftone, and it is dither-processed;

(3) when (dm(2), dm(3))=(1, 1), the input image is identified to be an edge part in the main scanning direction of a character, and it is binarized.

In the case of the present embodiment, the detection of the power pm(2) and pm(3) is sufficient for the identification of an input image, so that the image signal power detection section 6 comprises a power detector 602 at f2 in the main scanning direction and a power detector 603 at f3 in the main scanning direction, and the image identification section 7 comprises two pairs of comparators 11 and threshold value generators 12, and a coder 13 as shown in FIG. 20.

The combination of pm(2) and ps(3), that of ps(2) and ps(3) or that of ps(2) and pm(3) can be effective depending on the characteristics of a character, a photograph or a screen halftone.

Figure 21:
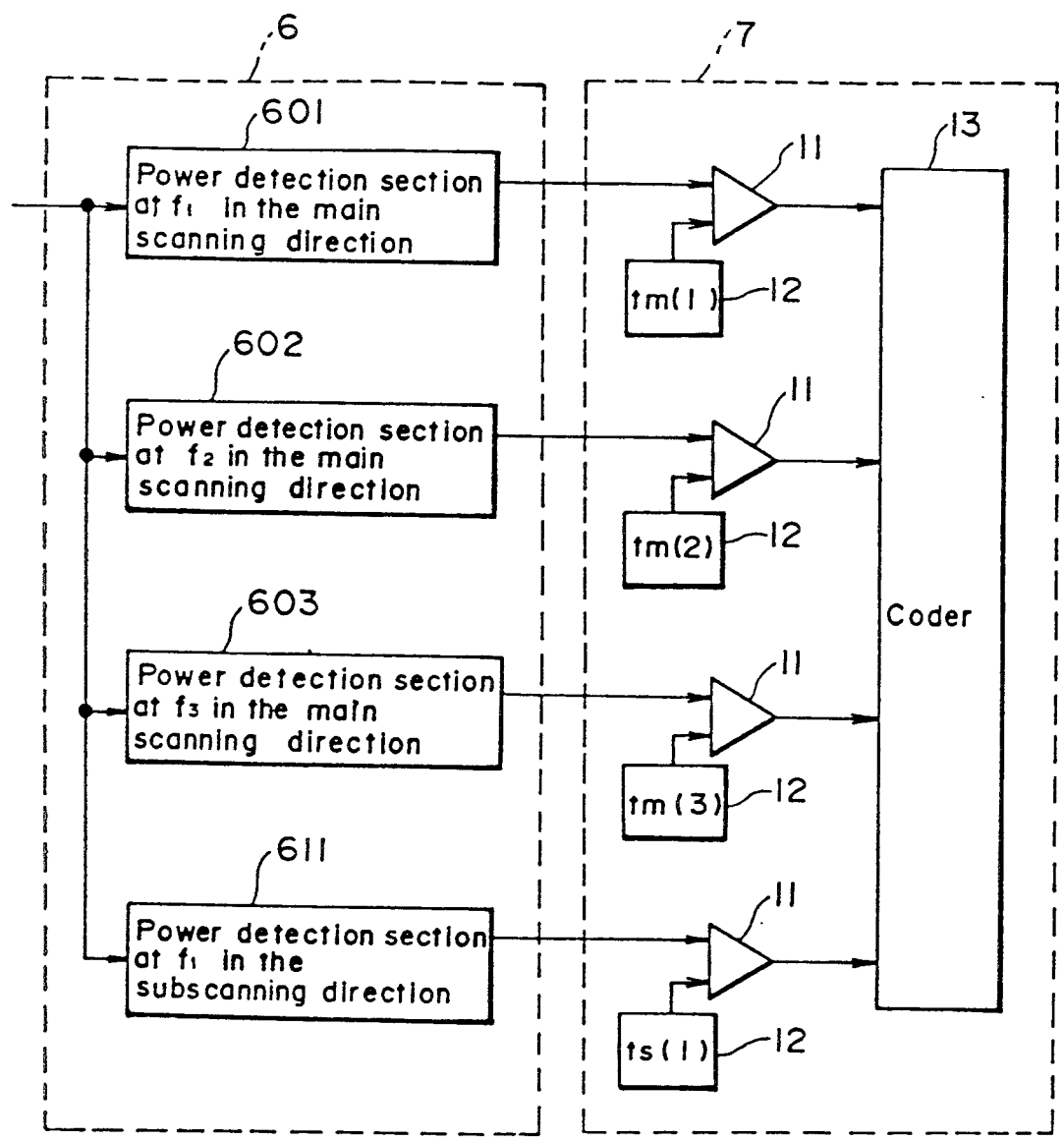
FIG. 21 is a detailed drawing of an image signal power detection section and an image identification section in a ninth embodiment.

A ninth embodiment is explained referring to FIG. 21. In the eighth embodiment, the discrimination among an edge part in the subscanning direction, a periodic pattern part in the subscanning direction and a periodic pattern part in the main scanning direction of a character is not possible. In the present embodiment the discrimination is effected as shown below and a proper process corresponding to the discrimination is executed.

The power pm(1) at a frequency f1 in the main scanning direction, the power ps(1) at a frequency f1 in the subscanning direction, and the power pm(2) at a frequency f2 and the power pm(3) at a frequency f3 in the main scanning direction have the following features.

|  | pm(1) | ps(1) | pm(2) | pm(3) |
|---|---|---|---|---|
| (1) Character | | | | |
| Flat part | small | small | small | small |
| Edge part in the main scanning direction | large | small | large | large |
| Edge part in the subscanning direction | small | large | small | small |
| Periodic pattern part in the main scanning direction | large | small | small | small |
| Periodic pattern part in the subscanning direction | small | large | small | small |
| (2) Photograph | | | | |
| Flat part | small | small | small | small |
| Edge part in the main scanning direction | small | small | large | small |
| Edge part in the subscanning direction | small | small | small | small |
| (3) Screen halftone | | | | |
| Flat part | large | large | small | small |
| Edge part in the main scanning direction | large | large | large | small |
| Edge part in the subscanning direction | large | large | small | small |

A proper process for each type of input images can be expressed as shown below using dm(1), ds(1), dm(2) and dm(3) as parameters, which are criterion values explained in the fourth embodiment:

(1) when (dm(1), ds(1), dm(2), dm(3)) =(0, 0, 0, X), the input image is identified to be a flat part of a character, a flat part of a photograph or an edge part of a photograph in the subscanning direction, and it is dither-processed;

(2) when (dm(1), ds(1), dm(2), dm(3)) =(0, 1, 0, X), the input image is identified to be an edge part in the subscanning direction or a periodic pattern part in the subscanning direction of a character, and it is binarized;

(3) when (dm(1), ds(1), dm(2), dm(3)) =(1, 0, 0, X), the input image is identified to be a periodic pattern part in the main scanning direction of a character;

(4) when (dm(1), ds(1), dm(2), dm(3)) =(1, 1, 0, X), the input image is identified to be a flat part or an edge part in the subscanning direction of a screen halftone, and it is dither-processed after a low-pass-process;

(5) when (dm(1), ds(1), dm(2), dm(3)) =(X, X, 1, 0), the input image is identified to be an edge part in the main scanning direction of a photograph or an edge part in the main scanning direction of a screen halftone, and it is dither-processed;

(6) when (dm(1), ds(1), dm(2), dm(3)) =(X, X, 1, 1), the input image is identified to be an edge part in the main scanning direction of a character, and it is binarized.

The expression "X" can be either 0 or 1.

In the case of the present embodiment, the power pm(1) at a frequency f1 in the main scanning direction, the power ps(1) at a frequency f1 in the subscanning direction, the power pm(2) at a frequency f2 in the main scanning direction and the power pm(3) at a frequency f3 in the main scanning direction are detected, so that image signal power detection section 6 comprises a power detector 601 at f1 in the main scanning direction, a power detector 602 at f2 in the main scanning direction, a power detector 603 at f3 in the main scanning direction and a power detector 611 at f1 in the subscanning direction, and the image identification section 7 comprises 4 pairs of comparators 11 and threshold value generators 12, and a coder 13 as shown in FIG. 21.

The combination of pm(1), ps(1), pm(2) and ps(3), the combination of pm(1), ps(1), ps(2) and ps(3), or the combination of pm(1), ps(1), ps(2) and pm(3) can be effective depending on the characteristic of a character, a photograph or a screen halftone.

Figure 22A:
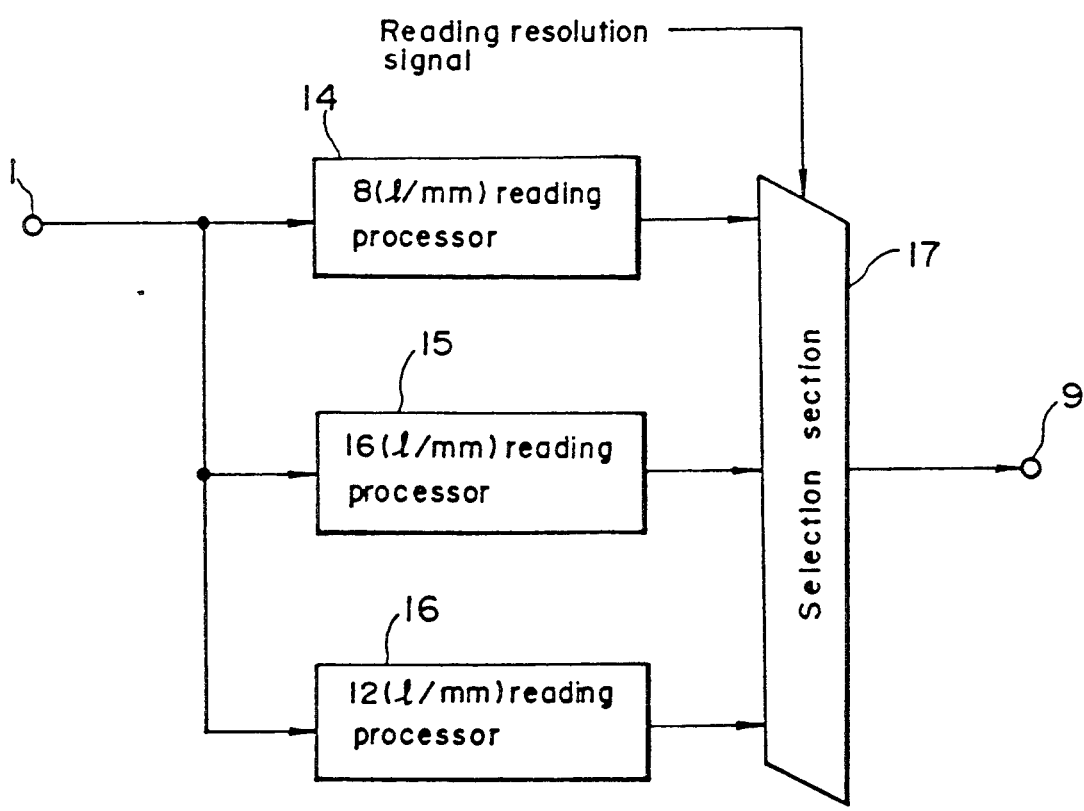
FIG. 22A is a drawing showing an image signal power detection section and an image identification section in a tenth embodiment.
Figure 22B:
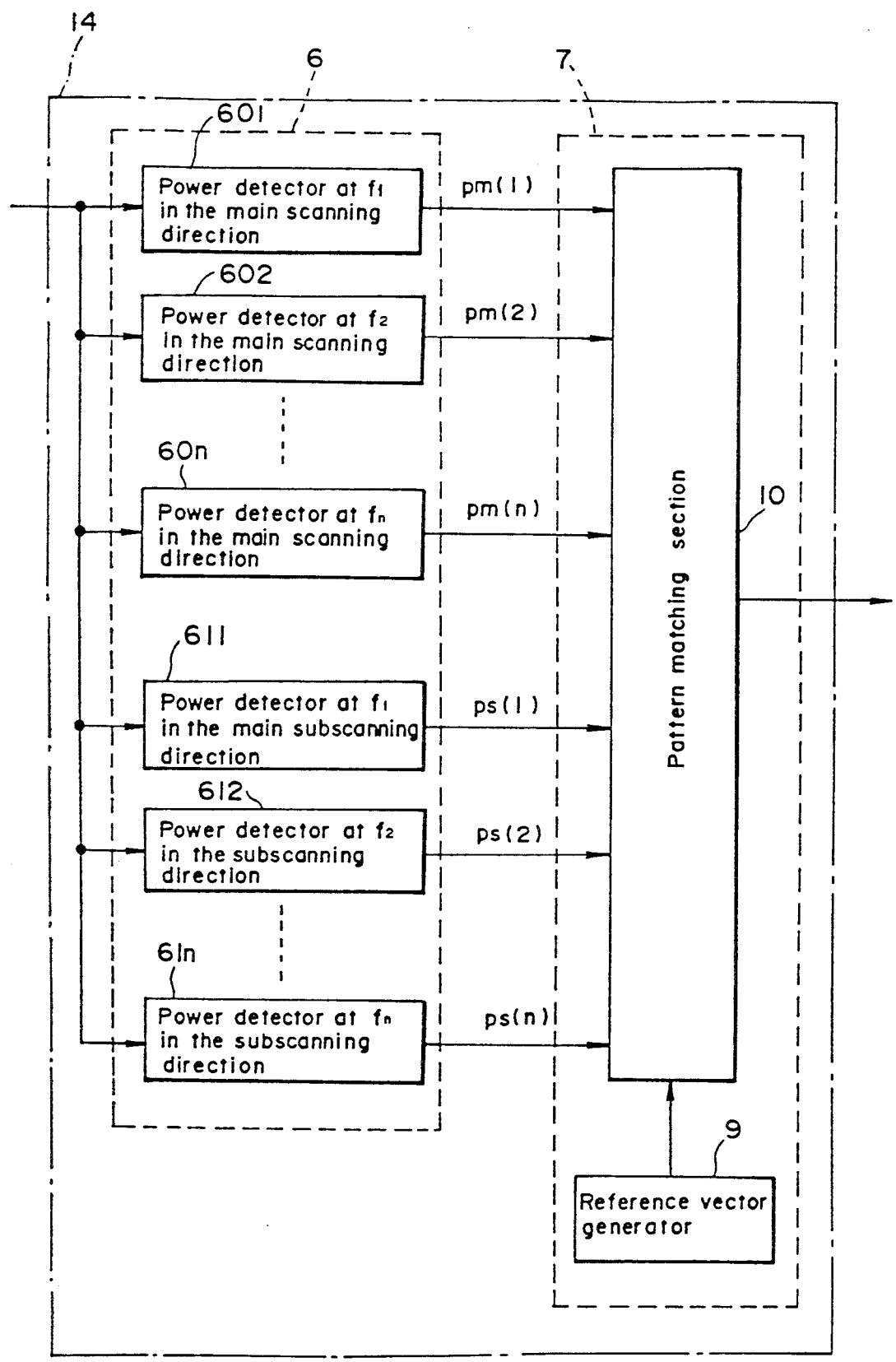
FIG. 22B is a detailed drawing of an image signal power detection section and an image identification section shown in FIG. 22A.

A tenth embodiment is explained referring to FIG. 22A and FIG. 22B. In the case of the output power pm(i) and ps(i) of the fi power detector 60i in the main scanning direction and the fi power detector 61i in the subscanning direction (i = 1 to n) which constitute the image signal power detection signal 6 shown in FIG. 2, when the reading resolution is changed in the course of creating an input image in reading a live picture and binarizing it, the frequency fi at which power is detected is changed.

For example, when a reading resolution is 8 (l/mm), the maximum picture frequency is 4 (lp/mm) (l: line, lp: line pair, mm: millimeter), when the reading resolution is 16 (l/mm), the maximum picture frequency is 8 (lp/mm). Because of this, the fi power detector 60i in the main scanning direction and the fi power detector 61i in the subscanning direction which are constituted to be used for the reading resolution of 8 (l/mm) cannot properly process an input image signal of 16 (l/mm).

In the present embodiment, a plurality of combinations of image signal power detection sections 6 and image identification sections 7 are adapted to correspond to the variety of reading resolutions at which input image signals are created and the output of a combination which matches to the reading resolution is arranged to be output to an output terminal 9. In FIG. 22A, a process section 14 for processing an input image signal of 8 (l/mm) reading resolution comprises a combination of an image signal power detection section 6 and an image identification section 7 for processing an input image signal digitized at the 8 (l/mm) reading resolution. A process section 15 for processing an input image signal of the 16 (l/mm) reading resolution comprises a combination of an image signal power detection section 6 and an image identification section 7 for processing an input image signal digitized at the 16 (l/mm) reading resolution. A process section 16 for processing an input image signal of a 12 (l/mm) reading resolution is similar to the above-mentioned processing sections.

A selection section 17 selects one from the combinations 14, 15 or 16 based on the reading resolution signal which is set by an operator.

FIG. 22B is a detailed drawing of the combination 14. This figure is similar to FIG. 2.

Figure 23A:
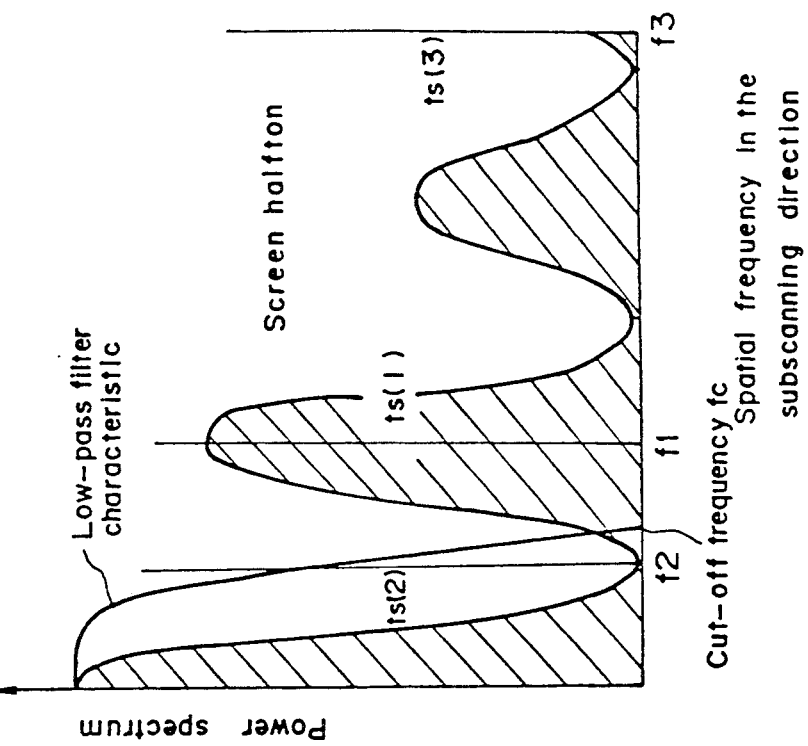
FIG. 23 is a characteristic chart of a low-pass filter in an eleventh embodiment.
Figure 23B:
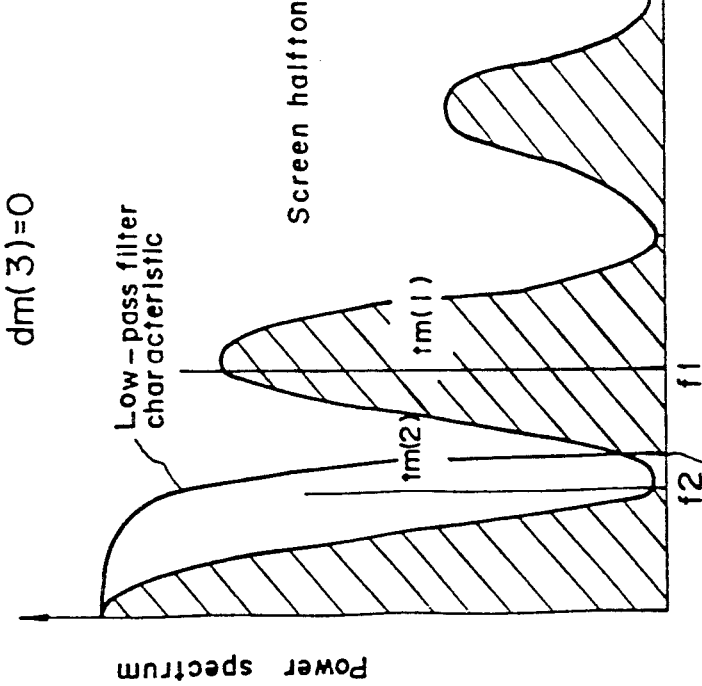

An eleventh embodiment is explained referring to FIG. 23. The low-pass filter section 2 shown in FIG. 1 and FIG. 14 removes the mesh point structure of a screen halftone and prevents the occurrence of moire stripes. It is effective to make the cut-off frequency fc of the low-pass filter section 2 lower than the fundamental frequency f1 of a screen halftone to remove the mesh point structure sufficiently.

FIG. 23 is a characteristic chart of a low-pass filter toward a spatial frequency distribution of a screen halftone.

Figure 24:
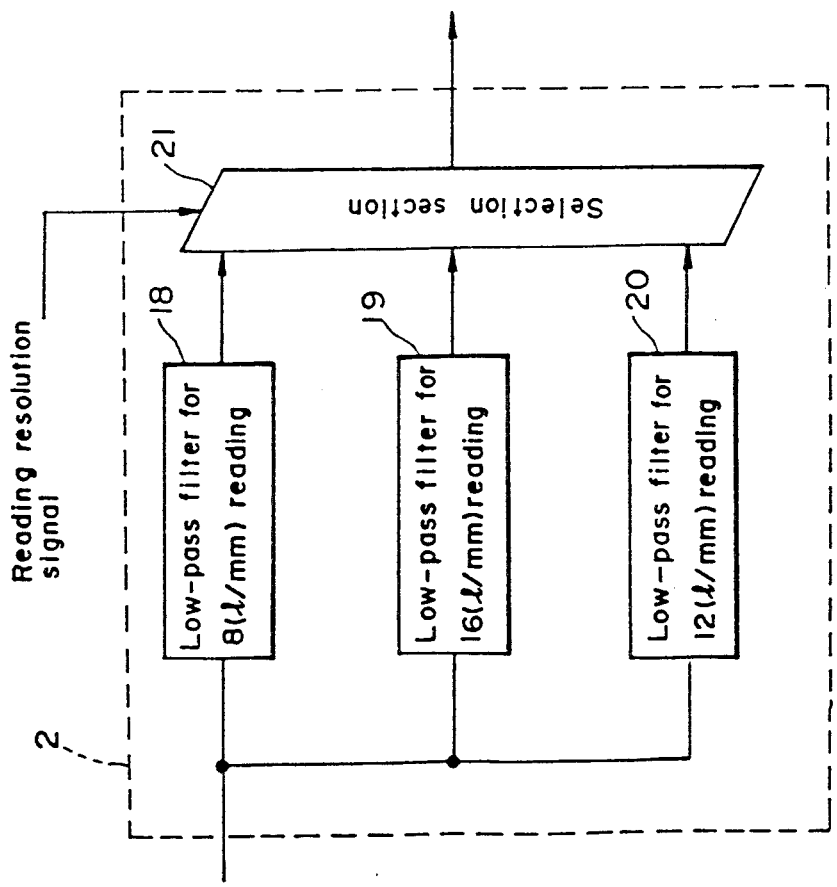
FIG. 24 is a drawing showing a low-pass filter in a twelfth embodiment.

A twelfth embodiment is explained referring to FIG. 24. The low-pass filter section 2 is constituted with a digital filter. Therefore when an input image signal digitized at the 16 (l/mm) reading resolution is input to a filter having a cut-off frequency fc which is set for an input image signal digitized at 8 (l/mm) reading resolution, the cut-off frequency fc is changed. The standard frequency which decides a cut-off frequency fc is a fundamental frequency f1 decided by a number of lines of a screen halftone as described in the eleventh embodiment. If the cut-off frequency fc of the low-pass filter section 2 is changed following the change of reading resolution, a proper filter process is not executed. In the present embodiment the low-pass filter section 2 is constituted with a plurality of low-pass filters corresponding to the reading resolution. In the FIG. 24, a low-pass filter 18 for a 8 (l/mm) reading resolution is a low-pass filter to be used for an input image signal digitized at the 8 (l/mm) reading resolution. A low-pass filter 19 for the 16 (l/mm) reading resolution and a low-pass filter 20 for the 12 (l/mm) reading resolution are similar to the above-mentioned filter 18. A selector 21 selects one from low-pass filters 18, 19 and 20 based on the reading resolution signal set by an operator.

Figure 25:
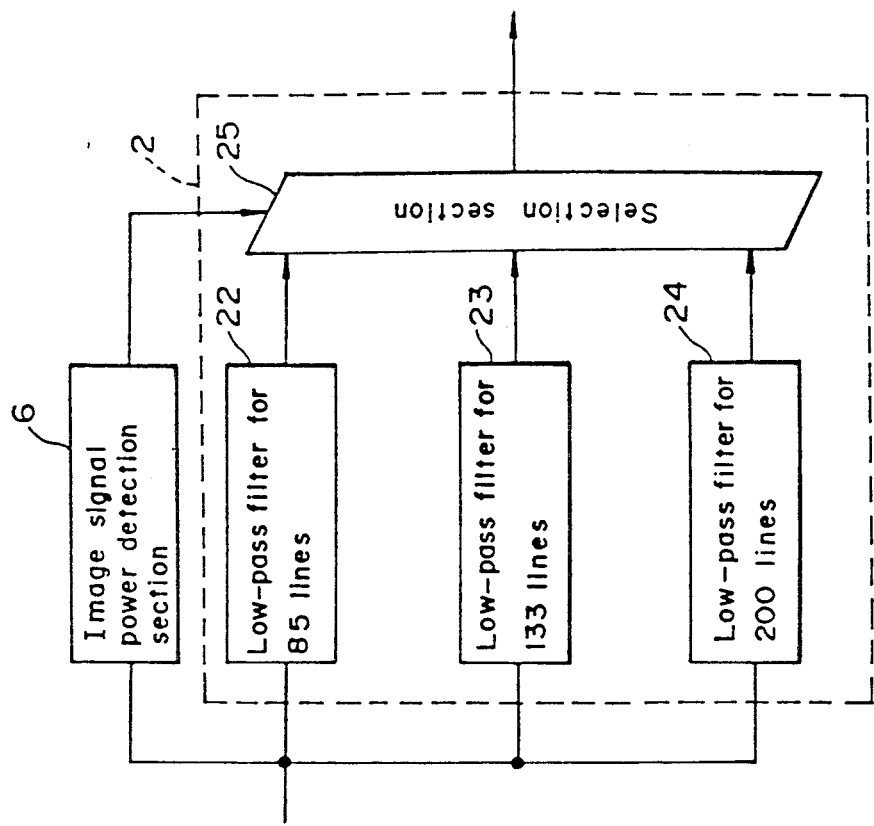
FIG. 25 is a drawing showing a low-pass filter in a thirteenth embodiment.

A thirteenth embodiment is explained referring to FIG. 25. The low-pass filter section 2 shown in FIG. 1 and FIG. 14 is provided to remove the mesh structure of a screen halftone. The cut-off frequency fc of the low-pass filter section 2 is decided by a fundamental frequency f1 which is decided by the number of lines of a screen halftone. Screen halftones having a variety of numbers of lines can be input as input image signals, therefore if the low-pass filters have the same cut-off frequency fc, when a screen halftone having a lower number of lines than the number of lines corresponding to the fc is input the mesh point structure is not sufficiently removed, and when a screen halftone having a higher number of lines is input a necessary part for the screen halftone is cut off and the played back image is blurred.

In the present embodiment, therefore, a plurality of low-pass filters corresponding to the numbers of lines of screen halftones to be input are provided in the low-pass filter section 2. In FIG. 25, a low-pass filter 22 for 85 lines is a low-pass filter corresponding to a screen halftone of 85 lines, and a low-pass filter 23 for 133 lines is a low-pass filter corresponding to a screen halftone of 133 lines. The image signal power detection section 6 outputs a number of lines signal of an input screen halftone, and a selection section selects a proper filter from low-pass filters 22, 23, 24 corresponding to the number of lines signal.

What is claimed is:

1. An image processor comprising:
    (a) an error diffusion processing means for processing an input image signal so as to cause the mean density of an input image to be equal to that of an output image by taking into account errors produced when the picture elements surrounding a given picture element are binarized according to the binarization of the given picture element, and for outputting a corresponding error diffusion processed image signal;
    (b) a binarization processing means for converting the input image signal into a binary image signal, and for outputting the binary image signal;
    (c) an image signal identification means for outputting an identification signal representative of a type of the input image signal based on a detected power level of the input image signal at each of at least one fixed frequency in at least one of a main scanning direction in which a read sensor for scanning image information of a document is arranged and a subscanning direction in which the read sensor is moved relative to the document; and (d) a selection means for outputting in accordance with the identification signal one of the error diffusion processed signal of said error diffusion processing means and the binary image signal of said binarization processing means.

2. An image signal processor comprising:

(a) a first processing means for carrying out a predetermined first quasi-tone reproduction process on an input image signal and for outputting a corresponding first processed image signal;

(b) a second processing means for low-pass filter processing the input image signal and for carrying out a predetermined second quasi-tone reproduction process on the thus low-pass filter processed input image signal and for outputting a corresponding second processed image signal;

(c) a binarization processing means for converting the input image signal into a binary image signal and for outputting the binary image signal;

(d) an image signal identification means for outputting an identification signal representative of a type of the input image signal based on a detected power level of the input image signal at each of at least one fixed frequency in at least one of a main scanning direction in which a read sensor for scanning image information of a document is arranged and a subscanning direction in which the read sensor is moved relative to the document, the detected power level obtained by Fourier transformation of the input image signal; and (e) a selection means for outputting in accordance with the identification signal one of the first processed image signal of said first processing means, the second processed image signal of said second processing means and the binary image signal of said binarization processing means.

3. An image signal processor according to claim 2, wherein the first and second quasi-tone reproduction processes are a dither process for quantizing the input image signal on the basis of a dither pattern produced repetitively and periodically.

4. An image signal processor according to claim 2, wherein the first and second quasi-tone reproduction processes are an error diffusion process for processing the input image signal to cause a mean density of an input image to be equal to that of an output image by taking into account errors produced when the picture elements surrounding a given picture element are binarized according to the binarization of the given picture element.

5. An image signal processor according to claim 1, 2, 3 or 4, wherein said image signal identification means outputs the identification signal based on a comparison between said power level and a prescribed threshold value.

6. An image signal processor according to claim 5, wherein the at least one fixed frequency is at least one of frequencies f1, f2 and f3 for each of the main scanning direction and the subscanning direction, where frequency f1 is a mesh point pitch frequency corresponding to a number of lines of a screen halftone, where frequency f2 is lower than the frequency f1 and is a frequency at which the power level of a screen halftone is at a minimum, and where frequency f3 is a maximum picture frequency determined by a reading resolution of the input image signal.

7. An image signal processor according to claim 6, wherein the at least one fixed frequency is the frequency f1 in the main scanning direction and the subscanning direction.

8. An image signal processor according to claim 7, wherein said image signal identification means comprises power detectors for individual f1 frequencies corresponding to a plurality of predetermined numbers of lines of screen halftones per unit length.

9. An image signal processor according to claim 6, wherein the at least one fixed frequency is the frequency f2 in the main scanning direction of said input image signal.

10. An image signal processor according to claim 6, wherein the at least one fixed frequency is the frequency f2 in the subscanning direction of the input image signal.

11. An image signal processor according to claim 6, wherein the at least one fixed frequency is the frequency f2 in the main scanning direction and the frequency f3 in the main scanning direction of the input image signal.

12. An image signal processor according to claim 6, wherein the at least one fixed frequency is the frequency f2 in the main direction and the frequency f3 in the subscanning direction of the input image signal.

13. An image signal processor according to claim 6, wherein the at least one fixed frequency in the frequency f2 in the subscanning direction and the frequency f3 in the subscanning direction of the input image signal.

14. An image signal processor according to claim 6, wherein the at least one fixed frequency is the frequency f2 in the subscanning direction and the frequency f3 in the main scanning direction of the input image signal.

15. An image signal processor according to claim 6, wherein the at least one fixed frequency is the frequency f1 in the main scanning direction and in the scanning direction, the frequency f2 in the main scanning direction and the frequency f3 in the main scanning direction of the input image signal.

16. An image signal processor according to claim 6, wherein the at least one fixed frequency is the frequency f1 in the main scanning direction and in the subscanning direction, the frequency f2 in the main scanning direction and the frequency f3 in the subscanning direction of the input image signal.

17. An image signal processor according to claim 6, wherein the at least one fixed frequency is the frequency f1 in the main scanning direction and in the subscanning direction, the frequency f2 in the subscanning direction and the frequency f3 in the subscanning direction of the input image signal.

18. An image signal processor according to claim 6, wherein the at least one fixed frequency is the frequency f1 in the main scanning direction and in the subscanning direction, the frequency f2 in the subscanning direction and the frequency f3 in the main scanning direction of the input image signal.

19. An image signal processor according to claim 1, 2, 3 or 4, wherein power value detection sections corresponding to a variety of resolutions of input image signals are provided in said image signal identification means, and wherein one of said power value detection sections is selected based on a predetermined reading resolution of the read sensor.

20. An image signal processor according to claim 2, 3 or 4 wherein the cut-off frequency of the low-pass filter processing is lower than the frequency f1 corresponding to the number of lines of a screen halftone.

21. An image signal processor according to claim 2, 3 or 4 wherein said second processing means includes a plurality of filters each corresponding to a resolution of the input image signal, and means for selecting one of the filters corresponding to a predetermined reading resolution.

22. An image signal processor according to claim 2, 3 or 4 wherein the second processing means includes filters corresponding to the numbers of lines of screen halftones, wherein the output of one of the filters corresponding to a detected frequency is selected, and wherein said identification means includes a detection means for detecting the detected frequency and a mesh point pitch frequency f1 corresponding to the number of lines of a screen halftone.

* * * * *